United States Patent
Gerhard et al.

(10) Patent No.: US 11,614,449 B2
(45) Date of Patent: Mar. 28, 2023

(54) T CELL RECEPTORS AND PEPTIDES DERIVED BY MUTATIONS FOR THE TREATMENT OF CANCER

(71) Applicant: TECHNISCHE UNIVERSITAET MUENCHEN, Munich (DE)

(72) Inventors: Markus Gerhard, Munich (DE); Dirk Busch, Munich (DE); Georg Doessinger, Munich (DE); Antonius Schumacher, Haarlem (NL); Carsten Linnemann, Amsterdam (NL)

(73) Assignee: TECHNISCHE UNIVERSITAET MUENCHEN, Munich (DE)

( * ) Notice: Subject to any disclaimer, the term of this patent is extended or adjusted under 35 U.S.C. 154(b) by 382 days.

(21) Appl. No.: 15/563,528

(22) PCT Filed: Mar. 31, 2016

(86) PCT No.: PCT/EP2016/057038
§ 371 (c)(1),
(2) Date: Sep. 29, 2017

(87) PCT Pub. No.: WO2016/156478
PCT Pub. Date: Oct. 6, 2016

(65) Prior Publication Data
US 2018/0088121 A1    Mar. 29, 2018

(30) Foreign Application Priority Data
Mar. 31, 2015   (EP) ................................. 15162015

(51) Int. Cl.
| | | |
|---|---|---|
| G01N 33/569 | (2006.01) | |
| G01N 33/574 | (2006.01) | |
| A61K 39/00 | (2006.01) | |
| A61K 39/02 | (2006.01) | |
| A61K 39/12 | (2006.01) | |
| C07K 14/47 | (2006.01) | |
| C12N 5/0783 | (2010.01) | |
| C12Q 1/6886 | (2018.01) | |

(52) U.S. Cl.
CPC .... *G01N 33/57492* (2013.01); *A61K 39/0011* (2013.01); *A61K 39/0208* (2013.01); *A61K 39/12* (2013.01); *C07K 14/4748* (2013.01); *C12N 5/0636* (2013.01); *C12N 5/0638* (2013.01); *C12Q 1/6886* (2013.01); *A61K 2039/5158* (2013.01); *C12N 2710/16134* (2013.01); *C12Q 2600/156* (2013.01); *G01N 33/56972* (2013.01); *G01N 2333/7051* (2013.01); *G01N 2333/70539* (2013.01)

(58) Field of Classification Search
None
See application file for complete search history.

(56) References Cited

U.S. PATENT DOCUMENTS

| 6,103,493 A | 8/2000 | Skerra et al. |
|---|---|---|
| 7,981,632 B2 | 7/2011 | Schmidt |
| 2017/0218042 A1* | 8/2017 | Tran ................ A61K 39/0011 |

FOREIGN PATENT DOCUMENTS

| EP | 0835934 B1 | 6/2010 | |
|---|---|---|---|
| EP | 2572725 A1 | 3/2013 | |
| WO | 1995/032731 A2 | 12/1995 | |
| WO | 02077018 A1 | 10/2002 | |
| WO | 2014076277 A1 | 5/2014 | |
| WO | WO-2014168874 A2 * | 10/2014 | ............. A61K 39/39 |

OTHER PUBLICATIONS

Lu et al. (Clin Cancer Res; 20(13); 3401-10)(2014). (Year: 2014).*
Fritsch et al. (OncoImmunology 3, e29311; Jun. 2014). (Year: 2014).*
Giannakis et al. (Nat Genet. Dec. 2014;46(12):1264-6, Supplemental pp. 1-2). (Year: 2014).*
Cieri et al., Blood. 2013;121(4):573-584, supplemental pp. 1-15. (Year: 2013).*
Maletzki et al. (European Journal of Cancer (2013) 49, 2587-2595). (Year: 2013).*
Reuschenbach et al. (Fam Cancer 2010;9: 173-9). (Year: 2010).*
Garbe et al. (Garbe et al. BMC Cancer 2011, 11:410). (Year: 2011).*
Schwitalle et al. (Gastroenterology 2008;134:988-997). (Year: 2008).*
Linnebacher et al. (J Biomed Biotechnol. 2010; 2010:841451). (Year: 2010).*
Starck et al., Cell. Mol. Life Sci. (2011) 68:1471-1479. (Year: 2011).*
Rizvi et al. (Science. Apr. 3, 2015;348(6230):124-8, supplemental pp. 1-31). (Year: 2015).*
Garbe et al. (PLoS ONE 6(11): e26517 (2011)). (Year: 2011).*
De Klerk et al., Trends in Genetics, Mar. 2015, vol. 31, No. 3, pp. 128-139, epublished Jan. 20, 2015. (Year: 2015).*
Office Action issued by EPO in European Application No. 16717271.7 dated Oct. 17, 2019.
Fritsch et al., Personal neoantigen cancer vaccines: The momentum builds. Oncoimmunology. Jun. 25, 2014;3:e29311 (3 pages).
Elderman et al., Acquired and intrinsic resistance in cancer immunotherapy. Mol Oncol. Sep. 12, 2014;8 (6):1132-1139.
Frajanoski et al., Somatically mutated tumor antigens in the quest for a more efficacious patient-oriented immunotherapy of cancer. Cancer Immunol Immunother Jan. 2015;64(1):99-104.
Van Buuren et al., High sensitivity of cancer exome-based CD8 T cell nee-antigen identification. Oncoimmunology. May 14, 2014;3:e28836 (6 pages).

(Continued)

*Primary Examiner* — Zachary S Skelding
(74) *Attorney, Agent, or Firm* — Acuity Law Group, PC; Michael A. Whittaker

(57) ABSTRACT

The present invention relates to a method for providing a neopeptide-specific T cell, wherein the neopeptide-specific T cell forms a complex having a half-life (T½) of at least 50 s with a neopeptide-MHC monomer. The present invention further relates to a T cell obtainable by the method as well as a pharmaceutical composition comprising such T cells.

18 Claims, 14 Drawing Sheets

Specification includes a Sequence Listing.

(56) References Cited

OTHER PUBLICATIONS

Anonymous, "Immunogenicity of colorectal cancer", Jan. 20, 2015 (Jan. 20, 2015), Retrieved from the Internet: URL http://icbi.at/CRCimmunity/.
Nauerth et al: "TCR-Ligand koff Rate Correlates with the Protective Capacity of Antigen-Specific CD8+ T Cells for Adoptive Transfer",Science Translational Medicine,vol. 5, No. 192, Jul. 3, 2013 (Jul. 3, 2013).
Hombrink et al: Mixed functional characteristics correlating with TCR-ligand k off-rate of MHC-tetramer reactive T cells within the naive T-cell repertoire 11 , European Journal of Immunology, vol. 43, No. 11, Nov. 25, 2013 (Nov. 25, 2013), pp. 3038-3050.
Weissbrich et al: "Adoptive immunotherapy", Oncoimmunology, vol. 2, No. 10, Oct. 1, 2013 (Oct. 1, 2013), page e26199.
Blankenstein et al: "Targeting cancer-specific mutations by T cell receptor gene therapy", Current Opinion in Immunology, vol. 33, Feb. 27, 2015 (Feb. 27, 2015), pp. 112-119.
International Search Report and Written Opinion issued in PCT/EP2016/057038 dated Jul. 14, 2016 (13 pages).
Ryan et al., "Tumor antigen epitopes interpreted by the immune system as self or abnormal-self differentially affect cancer vaccine responses", Cancer Res. Jul. 15, 2010; 70(14): 5788-5796. doi:10.1158/0008-5472.CAN-09-4519.
Aleksic et al., "Different affinity windows for virus and cancer-specific T-cell receptors—implications for therapeutic strategies", Eur J Immunol. Dec. 2012 ; 42(12): 3174-3179. doi:10.1002/eji.201242606.
Alexander-Miller et al., Selective expansion of high- or low-avidity cytotoxic T lymphocytes and efficacy for adoptive immunotherapy. Proc Natl Acad Sci U S A. Apr. 30, 1996;93(9):4102-4107.
Anderson et al., Parallel detection of antigen-specific T cell responses by combinatorial encoding of MHC multimers. Nat Protoc. Apr. 12, 2012;7(5):891-902.
Dossinger et al., MHC Multimer-Guided and Cell Culture-Independent Isolation of Functional T Cell Receptors from Single Cells Facilitates TCR Identification for Immunotherapy. PLoS One. Apr. 26, 2013;8(4):e61384 (11 pages).
Hadrup et al., Parallel detection of antigenspecific T-cell responses by multidimensional encoding of MHC multimers. Nat Methods. Jul. 2009;6(7):520-526.
DTU Bioinformatics, NetMHC 4.0 Server: Prediction of peptide-MHC class I binding using artificial neural networks (ANNs). Accessed online at: http://www.cbs.dtu.dk/services/NetMHC/. last modified Oct. 24, 2017.
Huang et al., T Cells Associated with Tumor Regression Recognize Frameshifted Products of the CDKN2A Tumor Suppressor Gene Locus and a Mutated HLA Class I Gene Product. J Immunol. May 15, 2004;172(10):6057-6064.
Jonsson et al., Real-Time Biospecific Interaction Analysis Using Surface Plasmon Resonance and a Sensor Chip Technology. Biotechniques. Nov. 1991;11(5):620-627.
Kono et al., Prognostic Significance of Adoptive Immunotherapy with Tumor-associated Lymphocytes in Patients with Advanced Gastric Cancer. Clin Cancer Res. Jun. 2002;8(6):1767-1771.
Linnemann et al., High-throughput epitope discovery reveals frequent recognition of neo-antigens by CD4+ T cells in human melanoma. Nat Med. Jan. 2015;21(1):81-85.
Lundegaard et al., NetMHC-3.0: accurate web accessible predictions of human, mouse and monkey MHC class I affinities for peptides of length 8-11. Nucleic Acids Res. Jul. 1, 2008;36(Web Server issue):W509-512.
Morgan et al., Cancer Regression in Patients After Transfer of Genetically Engineered Lymphocytes. Science. Oct. 6, 2006;314(5796):126-129.
Ozawa et al., Comprehensive analysis of the functional TCR repertoire at the single-cell level. Biochem Biophys Res Commun. Mar. 21, 2008;367(4):820-825.
Paitton et al., The Lungs as a Portal of Entry for Systemic Drug Delivery. Proc Am Thorac Soc. 2004;1(4):338-344.
Robbins et al., Tumor Regression in Patients With Metastatic Synovial Cell Sarcoma and Melanoma Using Genetically Engineered Lymphocytes Reactive With NY-ESO-1. J Clin Oncol. Mar. 1, 2011;29(7):917-924.
Rosenberg et al., Use of Tumor-Infiltrating Lymphocytes and Interleukin-2 in the Immunotherapy of Patients with Metastatic Melanoma. A preliminary report. N Engl J Med. Dec. 22, 1988;319(25):1676-1680.
Rosenberg et al., Durable Complete Responses in Heavily Pretreated Patients with Metastatic Melanoma Using T-Cell Transfer Immunotherapy. Clin Cancer Res. Jul. 1, 2011;17(13):4550-4557.
Smith-Garvin et al., T Cell Activation. Annu Rev Immunol. 2009;27:591-619.
Stemberger et al., Lowest numbers of primary CD8+ T cells can reconstitute protective immunity upon adoptive immunotherapy. Blood. Jul. 24, 2014;124(4):628-637.
Sun et al., Unbiased Analysis of TCRα/β Chains at the Single-Cell Level in Human CD8+ T-Cell Subsets. PLoS One. 2012;7(7):e40386 (11 pages).
Textoris-Taube et al., The T210M Substitution in the HLA-a*02:01 gp100 Epitope Strongly Affects Overall Proteasomal Cleavage Site Usage and Antigen Processing. J Biol Chem. Dec. 18, 2015;290(51):30417-30428.
Tran et al., Cancer Immunotherapy Based on Mutation-Specific CD4+ T Cells in a Patient with Epithelial Cancer. Science. May 9, 2014;344(6184):641-645.
Wolfel et al., A p16INK4a-Insensitive CDK4 Mutant Targeted by Cytolytic T Lymphocytes in a Human Melanoma. Science. Sep. 1, 1995;269(5228):1281-1284.
Lai et al., "RNF43 frameshift mutations contribute to tumourigenesis in right-sided colon cancer", Pathol Res Pract. Aug. 2019;215(8):152453. doi: 10.1016/j.prp.2019.152453. Epub May 13, 2019.
Malarkannan et al., "Presentation of out-of-frame peptide/MHC class I complexes by a novel translation initiation mechanism", Immunity. Jun. 1999;10(6):681-90. doi: 10.1016/s1074-7613(00)80067-9.
Koşaloğlu-Yalçin et al., "Predicting T cell recognition of MHC class I restricted neoepitopes", Oncoimmunology. Aug. 27, 2018;7(11):e1492508. doi: 10.1080/2162402X.2018.1492508.
Redmond et al., "Peripheral tolerance of CD8 T lymphocytes", Immunity. Mar. 2005;22(3):275-84. doi: 10.1016/j.immuni.2005.01.010.
Synder et al., "Genetic basis for clinical response to CTLA-4 blockade in melanoma", N Engl J Med. Dec. 4, 2014,371 (23):2189-2199. doi: 10.1056/NEJMoa1406498. Epub Nov. 19, 2014.
Xu and Zhang, "Mammalian Alternative Translation Initiation Is Mostly Nonadaptive", Mol. Biol. Evol. 37(7):2015-2028 doi:10.1093/molbev/msaa063.

* cited by examiner

| #pos Samples | Position | Peptide | Kd, nM | HLA-type | Frame |
|---|---|---|---|---|---|
| 13 | 141 | SLLPTCWAL | 7 | HLA-A02:01 | Deletionframe 212-418 |
| 13 | 135 | AMPTTTSLL | 178 | HLA-A02:01 | Deletionframe 212-418 |
| 13 | 142 | LLPTCWALPGV | 181 | HLA-A02:01 | Deletionframe 212-418 |
| 13 | 172 | ALGITASPEL | 400 | HLA-A02:01 | Deletionframe 212-418 |
| 9 | 55 | SLTSLRIEL | 101 | HLA-A02:01 | Deletion Frame 83-157 |
| 9 | 52 | VLSSLTSLRI | 192 | HLA-A02:01 | Deletion Frame 83-157 |
| 9 | 55 | SLTSLRIELL | 195 | HLA-A02:01 | Deletion Frame 83-157 |
| 7 | 148 | TQLARFFPI | 28 | HLA-A02:01 | Deletion Frame 527-699 |
| 7 | 152 | RFFPITPPV | 136 | HLA-A02:01 | Deletion Frame 83-157 |
| 6 | 39 | WLARLGWRV | 15 | HLA-A02:01 | Deletion Frame 527-699 |
| 6 | 92 | SLSQPLAQL | 136 | HLA-A02:01 | Deletion Frame 527-699 |
| 6 | 99 | QLTPPASAPV | 241 | HLA-A02:01 | Deletion Frame 527-699 |
| 6 | 42 | RLGWRVSEEPV | 347 | HLA-A02:01 | Deletion Frame 83-157 |
| 6 | 98 | AQLTPPASAPV | 373 | HLA-A02:01 | Deletion Frame 527-699 |
| 6 | 100 | LTPPASAPV | 435 | HLA-A02:01 | Deletion Frame 527-699 |
| 4 | 71 | SMAAVILSA | 24 | HLA-A02:01 | Deletion Frame 419-501 |
| 4 | 71 | SMAAVILSAA | 68 | HLA-A02:01 | Deletion Frame 419-501 |
| 4 | 28 | VLDGPPAPA | 227 | HLA-A02:01 | Deletion Frame 83-157 |
| 4 | 66 | SAYRGSMAAV | 475 | HLA-A02:01 | Deletion Frame 419-501 |
| 4 | 27 | RVLDGPPAPA | 479 | HLA-A02:01 | Deletion Frame 83-157 |
| 3 | 91 | YISIGLAPSA | 346 | HLA-A02:01 | Deletionframe 212-418 |
| 2 | 78 | ASMSSIVTV | 235 | HLA-A02:01 | Deletionframe 212-418 |
| 1 | 55 | AQPLCVPSV | 140 | HLA-A02:01 | Deletionframe 212-418 |

FIGURE 3

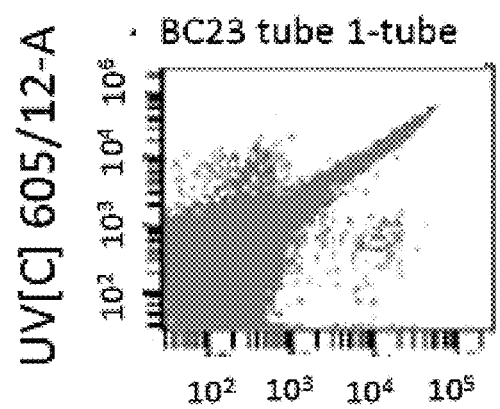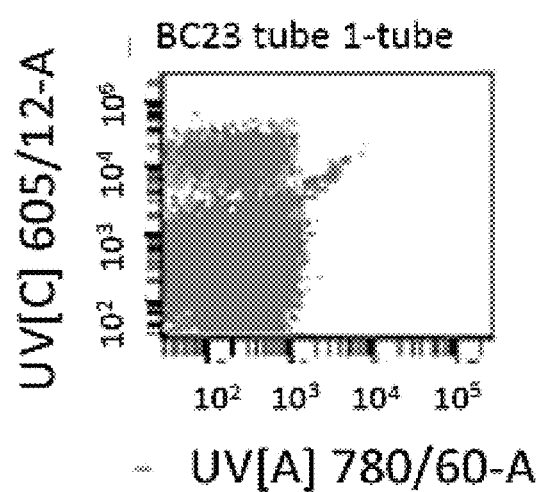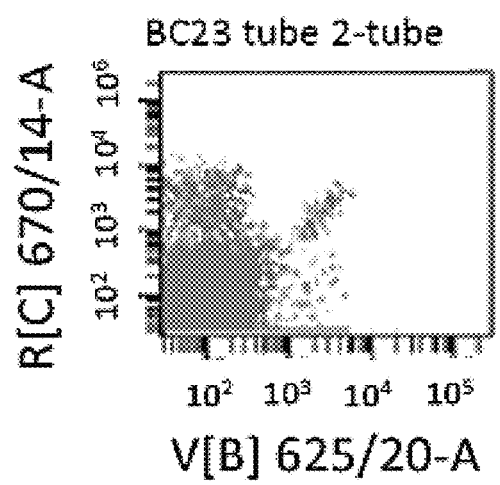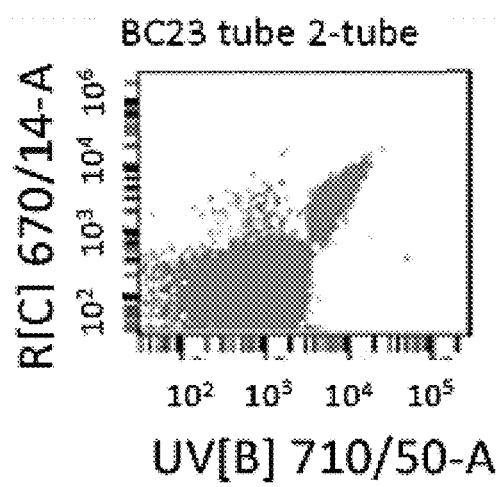
FIGURE 4 (CONT')

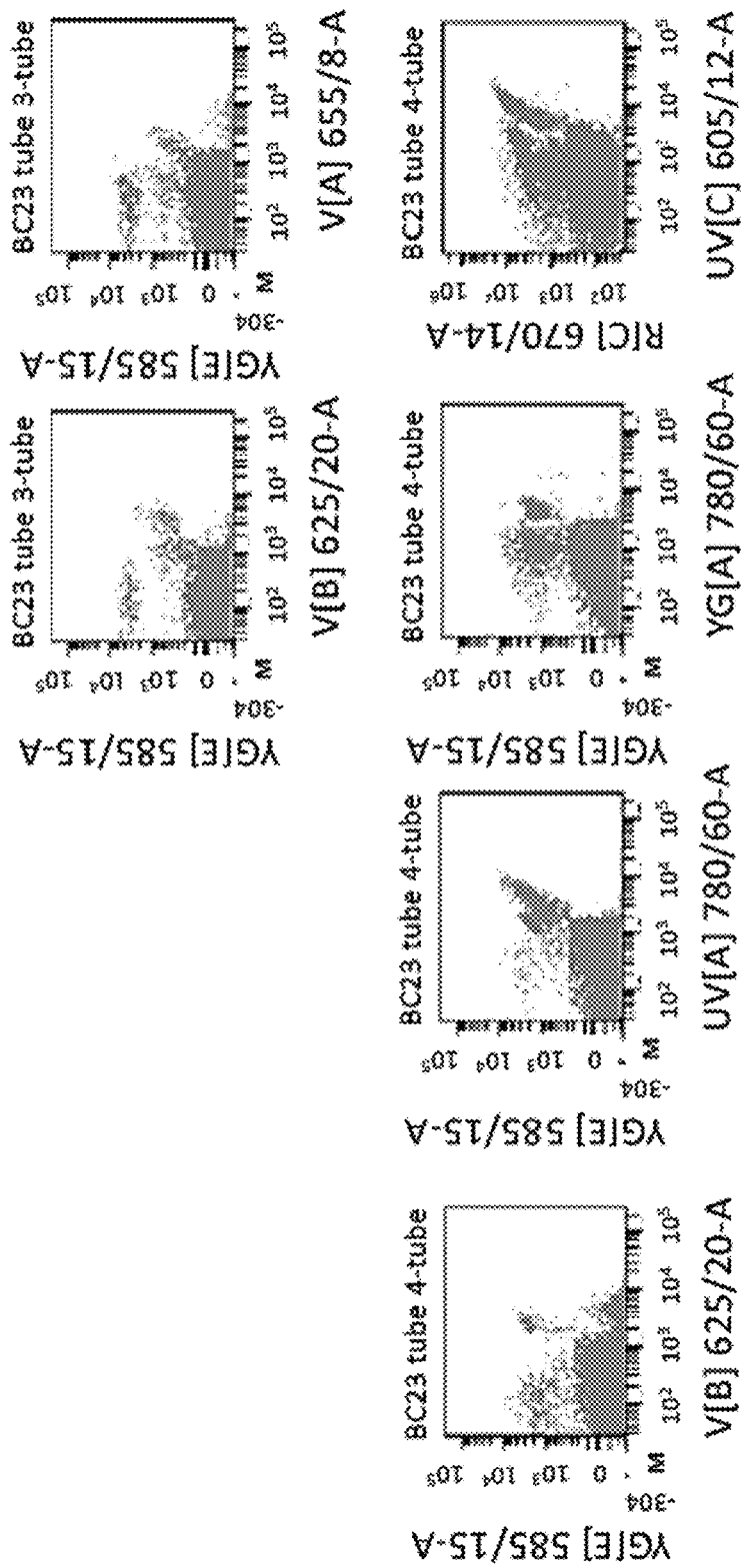
FIGURE 4 (CONT')

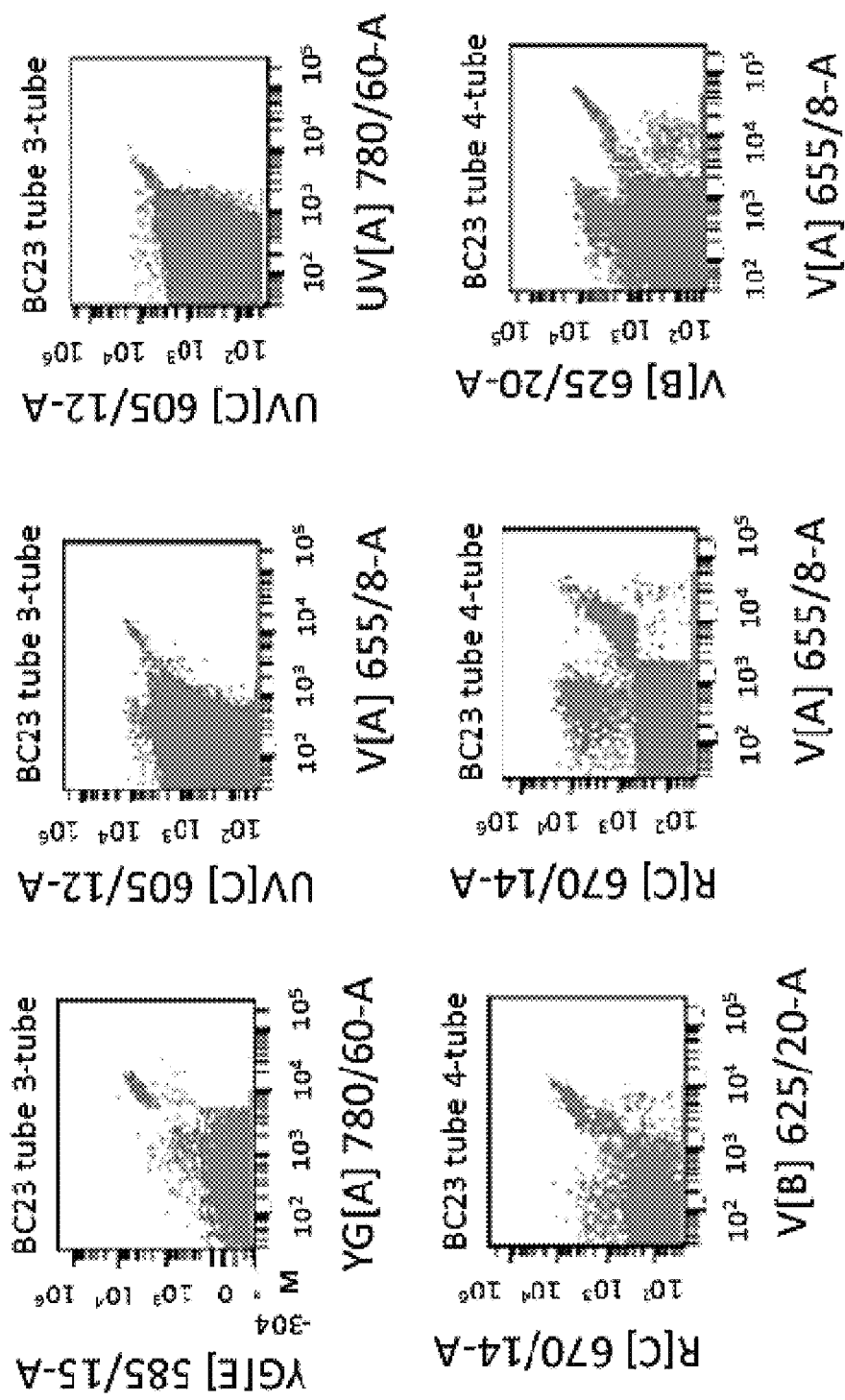
FIGURE 4 (CONT')

FIGURE 5

| V-Segmet | D-Segment | J-Segment | CDR3 |
|---|---|---|---|
| TRAV12-2*01 | | TRAJ13*01 | CALTGYQKVTF |
| TRBV7-9*01 | TRBD1*01 | TRBJ2-4*01 | CASSLVETDIQYF |

| V-Segmet | D-Segment | J-Segment | CDR3 |
|---|---|---|---|
| TRAV38-2/DV8*01 | | TRAJ43*01 | CAYIVNNNDMRF |
| TRBV6-5*01 | TRBD1*01 | TRBJ2-7*01 | CASSSWTGGYEQYF |

SEQ ID NO: 54: C ALTGYQKVTF
SEQ ID NO: 55: CASSLVETDIQYF
SEQ ID NO: 56: CAYIVNNNDMRF
SEQ ID NO: 57: CASSSWTGGYEQYF

FIGURE 7

| Peptide | K_D | Frame position | Frame type |
|---|---|---|---|
| RFFQMLILYYI | 346 | 1399 - 1431 | (-1) |
| FFQMLILYYI | 313 | 1399 - 1431 | (-1) |
| FQMLILYYI | 3 | 1399 - 1431 | (-1) |
| FQMLILYYIL | 22 | 1399 - 1431 | (-1) |
| QMLILYYIL | 158 | 1399 - 1431 | (-1) |
| LILYYILPRKV | 303 | 1399 - 1431 | (-1) |
| ALDKPCHQAEV | 372 | 1346 - 1398 | (-1) |
| ILYYILPRKV | 36 | 1399 - 1431 | (-1) |
| FLPCQQSHHV | 70 | 1496 - 1586 | (-1) |
| RLLQNYLHL | 121 | 1496 - 1586 | (-1) |
| YLHLWQGNQV | 55 | 1496 - 1586 | (-1) |
| HLWQGNQVSCL | 365 | 1496 - 1586 | (-1) |
| KVLQMDFLV | 17 | 1399 - 1431 | (-1) |
| RMYYFCHANKV | 106 | 1410 - 1425 | (+1) |
| RMYYFCHA | 631 | 1410 - 1425 | (+1) |
| YLKIKHLLL | 699 | 1346 - 1398 | (-1) |
| CVQTSTITK | 134 | 1426 - 1465 | (+1) |
| GMICHGCIV | 118 | 1496 - 1586 | (-1) |
| GMICHGCIVL | 241 | 1496 - 1586 | (-1) |
| FLFIQPEC | 364 | 1335 - 1360 | (+1) |
| LQMDFLVHPA | 20 | 1399 - 1431 | (-1) |
| QMDFLVHPA | 55 | 1399 - 1431 | (-1) |

FIGURE 11

β2-MICROGLOBULIN (PROTEIN SEQUENCE/UNIPROT: P61769)
MSRSVALAVLALLSLSGLEA(SIGNAL PEPTIDE/SEQ ID NO: 51)-

IQRTPKIQVYSRHPAENGKSNFLNCYVSGFHPSDIEVDLLKNGERIEKVEHSDLSFSKDWSFYLLYYTEFTPTEKDEYA
CRVNHVTLSQPKIVKWDRDM (SEQ ID NO: 52)

FIGURE 12

| Peptide | Length | neoORF (n+) | HLA type | Predicted affinity (Kd, nM) | Mutations in literature | in vitro processed |
|---|---|---|---|---|---|---|
| HPRSQAWAL (SEQ ID NO: 58) | 9 | 1 | HLA-B0702 | 5 | R27fs, K145fs, R40fs, S41fs, E43fs, L65fs, A115fs, R117fs, C119fs, P192fs, R225fs, Q254fs, S264fs, C275fs | 11mer, 12mer, 14mer |
| VPSVWRSSL (SEQ ID NO: 59) | 9 | 1 | HLA-B0702 | 6 | R27fs, K145fs, R40fs, S41fs, E43fs, L65fs, A115fs, R117fs, C119fs, P192fs, P195fs, R225fs, Q254fs, S264fs | epitope, 10mer, 11mer |
| IPAMPTTTSL (SEQ ID NO: 60) | 10 | 1 | HLA-B0702 | 6.5 | R27fs, K145fs, R40fs, S41fs, E43fs, L65fs, A115fs, R117fs, C119fs, P192fs, P195fs, R225fs, Q254fs, S264fs, C275fs | 13mer, 14mer |
| SLLPTCWAL (SEQ ID NO: 1) | 9 | 1 | HLA-A0201 | 7 | R27fs, K145fs, R40fs, S41fs, E43fs, L65fs, A115fs, R117fs, C119fs, P192fs, P195fs, R225fs, Q254fs, S264fs, C275fs | epitope |
| RPAAGRPGV (SEQ ID NO: 61) | 9 | 1 | HLA-B0702 | 13.2 | R27fs, K145fs, R40fs, S41fs, E43fs, L65fs, A115fs, R117fs, C119fs, P195fs, R225fs, | 12mer, 14mer |
| APGRSPAPL (SEQ ID NO: 62) | 9 | 2 | HLA-B0702 | 15 | A33fs, K54fs, L88fs, R117fs, R119fs, L311fs, R363fs, K45fs, L61fs, F69fs, P195fs, | epitope |
| HPRSQAWAL (SEQ ID NO: 58) | 9 | 1 | HLA-B0801 | 17.7 | see above | see above |

T CELL RECEPTORS AND PEPTIDES DERIVED BY MUTATIONS FOR THE TREATMENT OF CANCER

CROSS-REFERENCE TO RELATED APPLICATIONS

The present invention is filed under 35 U.S.C. § 371 as the U.S. national phase of International Application No. PCT/EP2016/057038, filed Mar. 31, 2016, which designated the U.S. and claims priority benefit to European Patent Application No. 15162015.0, filed Mar. 31, 2015. The entire disclosure of the above-identified priority applications is hereby fully incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 29, 2017, is named SCH3900US_SeqListing.txt and is 14 kilobytes in size.

FIELD OF THE INVENTION

The present invention relates to a method for providing a neopeptide-specific T cell, wherein the neopeptide-specific T cell forms a complex having a half-life ($T_{1/2}$) of at least 50 s with a neopeptide-MHC monomer. The present invention further relates to a T cell obtainable by the method as well as a pharmaceutical composition comprising such a T cell.

BACKGROUND

The transfusion of lymphocytes, referred to as T cell therapy, is being tested for the treatment of cancer and chronic infections. T cell therapy has the potential to enhance antitumor immunity, augment vaccine efficacy, limit graft-versus-host and autoimmune disease. Two fundamentally different strategies to stimulate antitumor immunity have been tested in humans: therapeutic vaccination and passive immunization. Passive immunization, herein referred to as T cell therapy, is the transfusion of autologous or allogeneic T cells into tumor-bearing hosts, i.e., patients.

A principal limitation of such T cell therapy for some tumors is that the tumors are poorly immunogenic; therefore, neither T cells with high avidity for tumor-specific antigens, nor T cells with the desired specificity remain in the patient following chemotherapy. One strategy to overcome this limitation is that T cells are being transduced to express natural αβTCR heterodimers of known specificity and avidity for tumor antigens. Another strategy is directed at the identification of tumor specific T cells from a subject, which can then be expanded and re-introduced in a subject.

One way to improve tumor-specificity of T cells is to provide T cells comprising a TCR, which is specific for tumor suppressor genes. These genes are important guardians preventing the malignant transformation of cells and thus the development of tumors. Different publications identified peptides, the so called neopeptides, arising from frame shift or point mutations. These neopeptides are highly specific for tumors. Until now, however, such neopeptides have been mainly proposed as targets for therapeutic vaccination strategies. For example, European Patent Application EP 2 572 725 A1 describes a vaccine for prevention and treatment of cancer characterized by microsatellite instability (MSI). Yet, a therapeutic potential of neopeptides in passive immunization has so far not been explored. In addition, Huang et al, J Immunol 2004; 172:6057-6064 describe T Cells associated with tumor regression recognize frameshifted products of the CDKN2A tumor suppressor gene locus and a mutated HLA Class I gene product.

The technical problem of the present invention can therefore be seen in the provision of an improved T cell therapy, and in particular passive immunization.

This problem is solved by the embodiments reflected in the claims, described in the description, and illustrated in the Examples and Figures of the present application.

SUMMARY OF THE INVENTION

The above being said, the present invention relates to a method for providing a neopeptide-specific T cell, wherein the neopeptide-specific T cell forms a complex having a half-life ($T_{1/2}$) of at least 50 s with a neopeptide-MHC monomer, wherein said neopeptide is derived from a mutation in a tumor suppressor gene, the method comprising:
a) contacting T cells with a detectably labeled neopeptide-MHC complex
b) isolating a T-cell, which comprises a T cell receptor (TCR) that specifically binds to the neopeptide-MHC complex; and
c) determining the $T_{1/2}$ by measuring the signal of the detectable label comprised in the MHC monomer over a period of time.

In some embodiments, step b) of the method of the present invention further comprises
b.1) isolating the neopeptide-specific TCR;
b.2) determining the TCR α chain and β chain sequences;
b.3) recombinantly expressing the neopeptide-specific TCR in a T cell.

The present invention further relates to a T cell capable of binding a neopeptide that is derived from a mutation in a tumor suppressor gene, wherein the binding complex of the T cell formed with the neopeptide-MHC complex has a half-life ($T_{1/2}$) of at least 50 s, wherein the T cell is obtainable by the method of the present invention.

The present invention also relates to the T cell of the present invention for use in tumor specific T cell activation.

In addition, the present invention relates to the T cell of the present invention for use in tumor cell killing.

Furthermore, the present invention relates to a pharmaceutical composition comprising the T cell of the present invention.

The present invention also relates to a TCR comprising a sequence of any of SEQ ID NO. 54-SEQ ID NO. 57.

The present invention also relates to a neopeptide of any of SEQ ID NO. 1-SEQ ID NO. 45.

Also, the present invention relates to a use of the T cell of the present invention or the pharmaceutical composition of the present invention in the manufacture of a medicament for treating a subject having a disease, preferably cancer.

The present invention furthermore relates to a method of treating cancer in a subject, comprising the step of administering the T cell of the present invention or the pharmaceutical composition of the present invention to a subject in need thereof.

Figure 1:
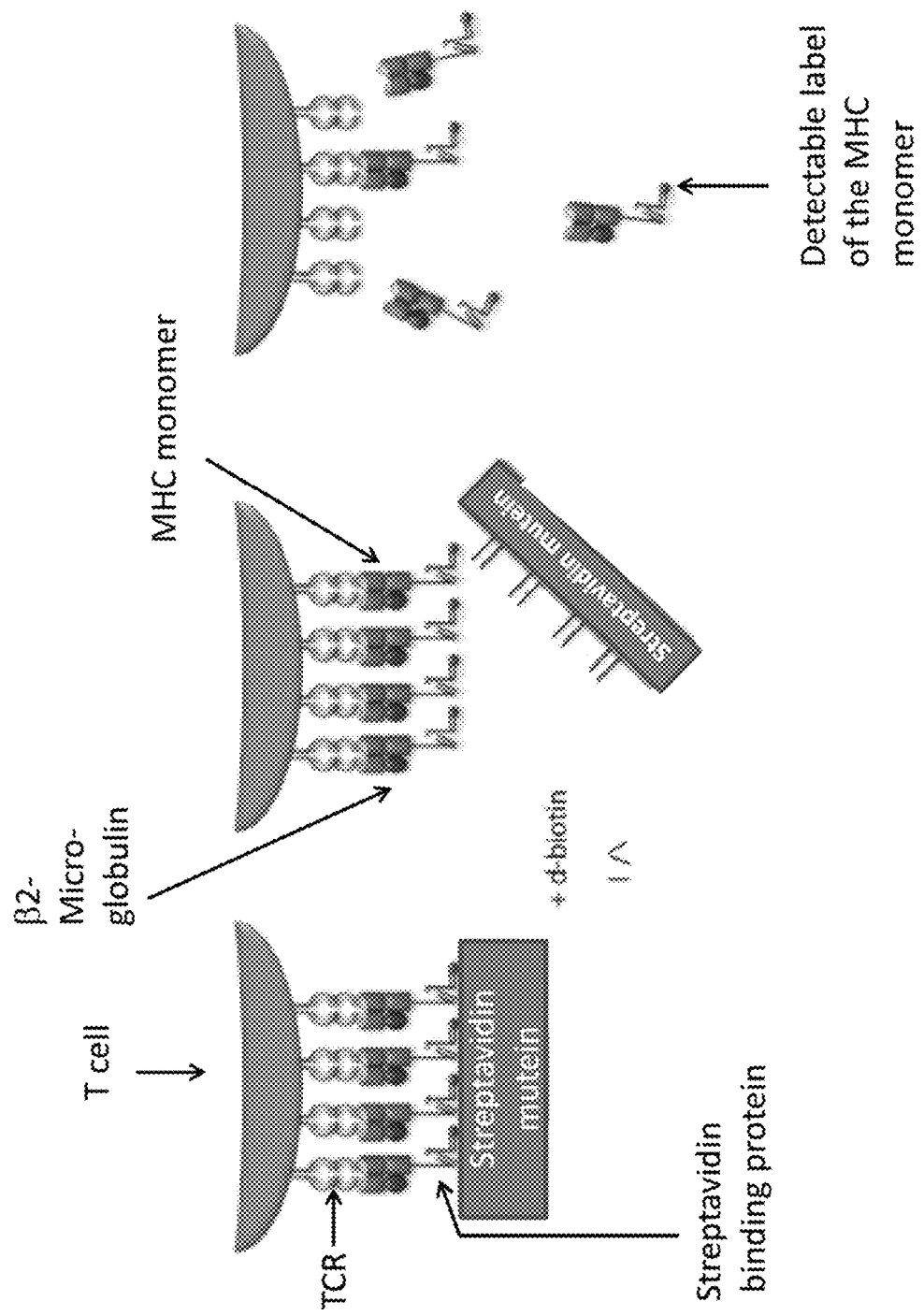
FIG. 1 depicts a method of obtaining the $T_{1/2}$ of neopeptide-specific T cells of the present invention. The method of FIG. 1 is carried out in accordance with the protocol described in Nauerth M et al. (2013) "TCR-ligand koff rate correlates with the protective capacity of antigen-specific CD8+ T cells for adoptive transfer." Sci Transl Med. 3; 5(192):192. While Nauerth et al describe the characterization of cytomegalovirus (CMV)-specific T cells, for the characterization of the T cell of the present invention neopeptide-MHC monomer dissociation experiments are conducted for the determination of $T_{1/2}$. Such a neopeptide-MHC monomer can be a MHC class I molecule. The MHC monomer can also be modified in different ways. For example, it can comprise a β2-microglobulin as described herein. The MHC monomer can also be truncated at the transmembrane region. Furthermore, the MHC monomer can comprise a streptavidin binding peptide, which binds to a streptavidin mutein as described herein. The streptavidin binding peptide can be fused or conjugated anywhere to the MHC monomer. The MHC monomer also comprises a detectable label as described herein. The detectable label can be attached anywhere to the MHC molecule or e.g. to the streptavidin binding peptide. Preferably, the detectable label does not interfere with TCR binding of the MHC monomer.

The MHC monomer is then used in dissociation experiments, which can be a reversible staining method. A reversible staining method can include a multivalent binding complex formation (multimerization) between e.g. a streptavidin-mutein and a neopeptide-MHC monomer comprising e.g. a streptavidin binding peptide (FIG. 1 picture on the left hand side). One multimerization reagent that comprises at least one or two binding sites for reversibly binding a streptavidin binding peptide is a streptavidin mutein such as the streptavidin muteins "1" and "2" that are known from U.S. Pat. No. 6,103,493 or European Patent 0 835 934 and are commercially available from IBA GmbH under the trademark "Strep-Tactin®". In this way a neopeptide-specific MHC monomer that binds to neopeptide-specific T cell can be reversibly multimerized by complex formation between e.g. a streptavidin mutein such as "Strep-Tactin®" and a streptavidin binding peptide such as Trp-Arg-His-Pro-Gln-Phe-Gly-Gly (SEQ ID NO: 46), Trp-Ser-His-Pro-Gln-Phe-Glu-Lys (SEQ ID NO: 47), Trp-Ser-His-Pro-Gln-Phe-Glu-Lys-(GlyGlyGlySer)$_3$-Trp-Ser-His-Pro-Gln-Phe-Glu-Lys (SEQ ID NO: 48), or Trp-Ser-His-Pro-Gln-Phe-Glu-Lys-(GlyGlyGlySer)$_2$-Trp-Ser-His-Pro-Gln-Phe-Glu-Lys (SEQ ID NO: 49) (see also FIG. 1, picture on the left hand side).

Neopeptide-specific T cells can then be stained with the multivalent binding complex and can optionally be separated from other cells that are devoid of a neopeptide-specific TCR, for example, by fluorescence-activated cell sorting (also known under the trademark "FACS™"). Subsequent treatment of isolated stained neopeptide-specific T cells with the D-biotin that is the natural ligand of streptavidin and competes with the (binding) of the streptavidin binding peptide. This competitive binding causes displacement of the neopeptide-specific monomers from the multimerization reagent, thereby releasing the multimerization reagent (the streptavidin mutein such as a Strep-Tactin® complex) from the neopeptide-specific T cell (FIG. 1, picture in the middle).

Remaining neopeptide-specific MHCs, uncomplexed from the streptavidin mutein (Strep-Tactin®), remain bound to surface expressed TCRs until they (spontaneously) dissociate in a reasonable time window due to their high $k_{off}$ rate. This $k_{off}$ rate can then be measured e.g. via measuring the decay of a detectable label. In most cases the signal of detectable label will decrease over time due to dissociation of the MHC-TCR complex (FIG. 1, picture on the right hand side).

Figure 2:
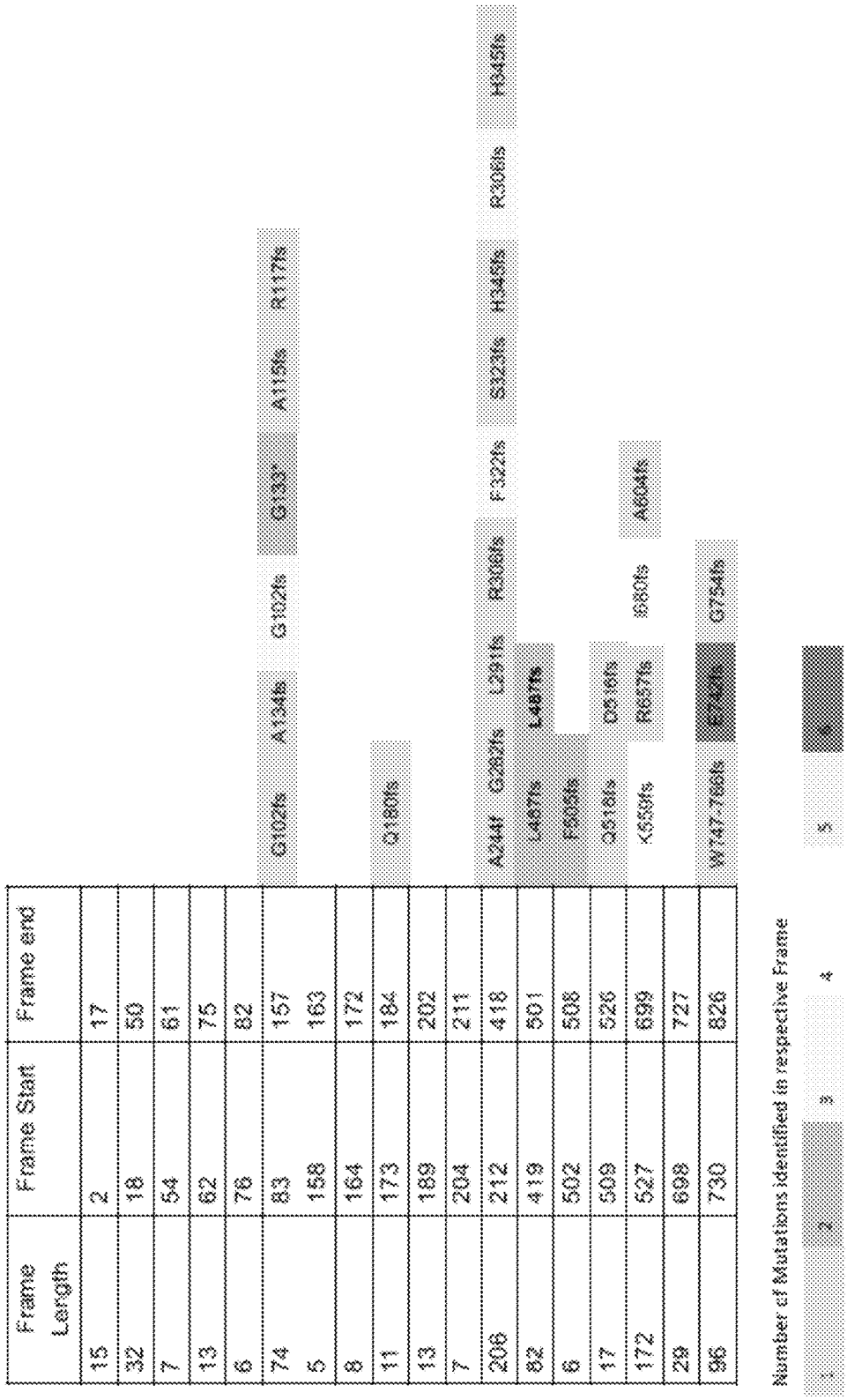

FIG. 2 shows a map of frameshift mutations in the RNF43 gene-locus detected by deep sequencing of colon cancer samples. The deep sequencing was directed to the genomic DNA present in individual samples. In a first step the genomic DNA is fragmented into a library of small segments that can be uniformly sequenced in many parallel reactions.

Theoretical reading frames that can be derived by deletion of one DNA nucleotide ((N*3)−1), two DNA nucleotides ((N*3)−2), or any number of nucleotides((N*3)−X), respectively one ((N*3)+1) or two insertions ((N*3)+2) or any number of insertions ((N*3)+X). The table shows the length of all such potential frames with mutation events from a deep sequencing dataset assigned to the respective frame.

FIG. 3 depicts a representative list of potential epitopes derived from the NetMHC prediction algorithm (3.4). The NetMHC 3.4 server predicts binding of peptides to a number of different HLA alleles. NetMHC qualifies the probability of the presentation of a given peptide via the respective MHC complex by calculating a theoretical binding strength between the peptide and the HLA complex. The definition of the theoretical neo-reading frames and the assignment of the peptides has already been performed before data are presented to the algorithm. This algorithm can be used via the webpage http://www.cbs.dtu.dk/services/NetMHC/. Information about the theoretical binding strength between the peptide and the HLA complex (indicated as $K_d$ value in the table in FIG. 1B), HLA-restriction and neopeptide sequences assigned to their respective reading frames and position within the frames are listed. As can be seen in FIG. 2 all identified peptides are predicted to bind to the HLA-type HLA-A02:01.

Figure 4:
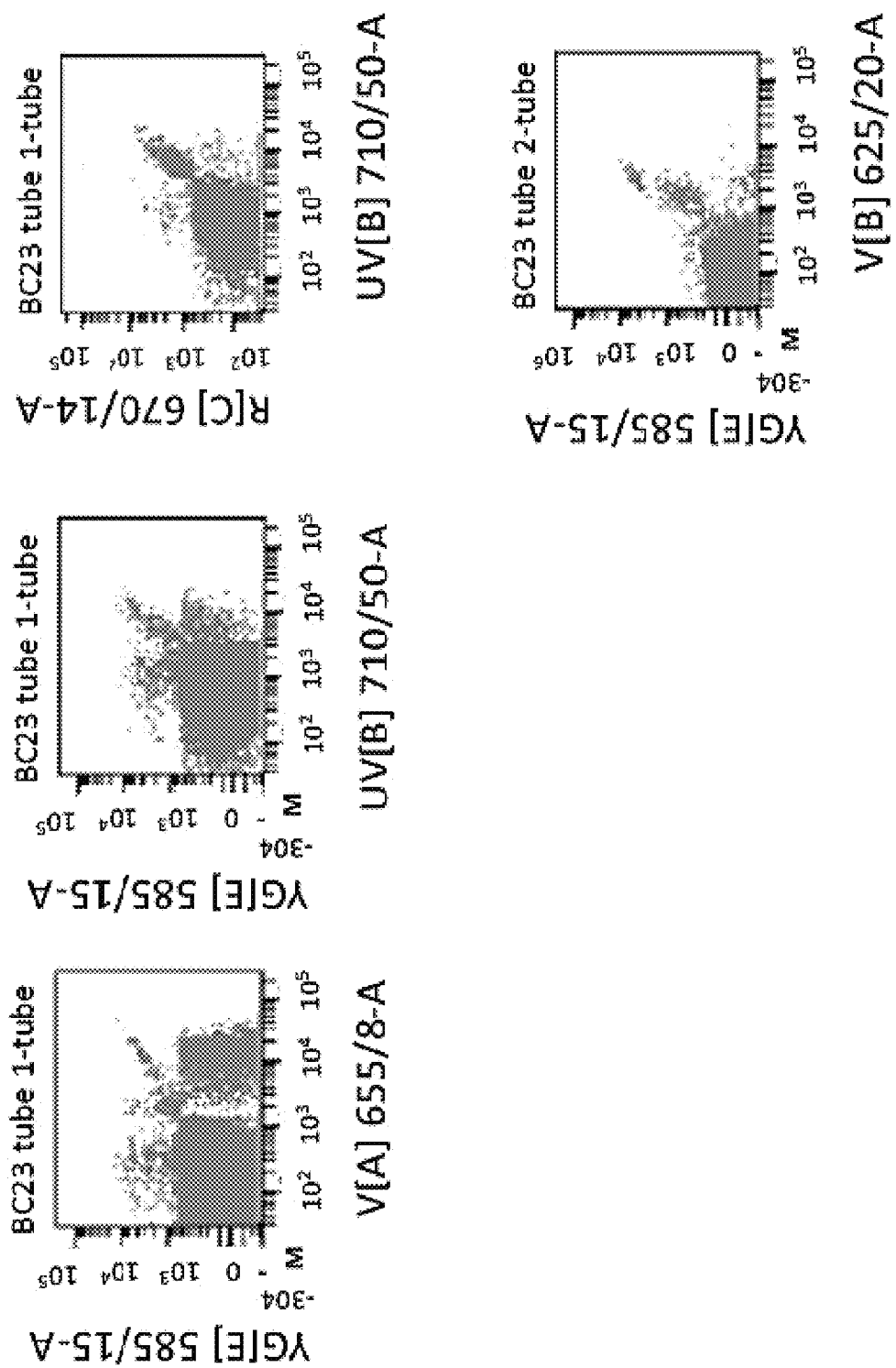

FIG. 4 shows RNF43 frameshift neopeptide specific T cell populations that were labeled with Peptide-MHC multimers after 2 weeks of in vitro expansion. Double positive populations in FACS plots are specifically stained.

FIG. 5 depict two T cell receptor sequences from T cells against the potential RNF43 Epitope RVLDGPPAPA that have been analyzed for their subdomain usage and their amino acid sequence of their main specificity determining CDR3 domain. Also depicted are the V-, D- and J-segment.

Figure 6:
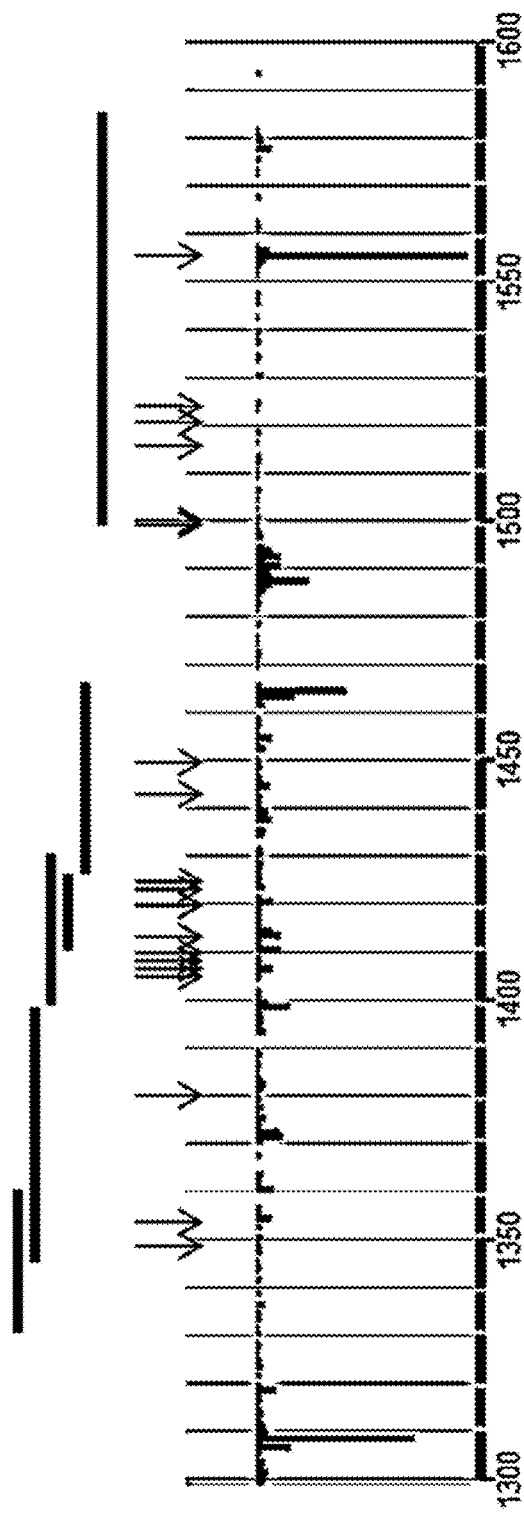

FIG. 6 is a map of frameshift mutations in the APC-tumor suppressor gene. The histogram depicts the distribution of all mutations, which are publically available through the COSMIC database v71 (http://cancer.sanger.ac.uk/cancergenome/projects/cosmic/). Theoretical reading frames that can be derived by deletion of one DNA nucleotide or any number of nucleotides (N*3)+1, respectively two insertions or any number of insertions (N*3)+2. Reading frames that harbor significant numbers of frameshift mutations were selected for further experiments. Lines above the histogram visualize these (−1)-frames (light grey), respectively (+1)-frames (dark grey). Grey arrows indicate the position of predicted HLA-A2 restricted epitopes.

FIG. 7 shows a representative list of HLA-A2 restricted potential neopeptides derived from the NetMHC prediction algorithm in theoretical shifted reading frames in the Tumor suppressor gene APC.

Figure 8:
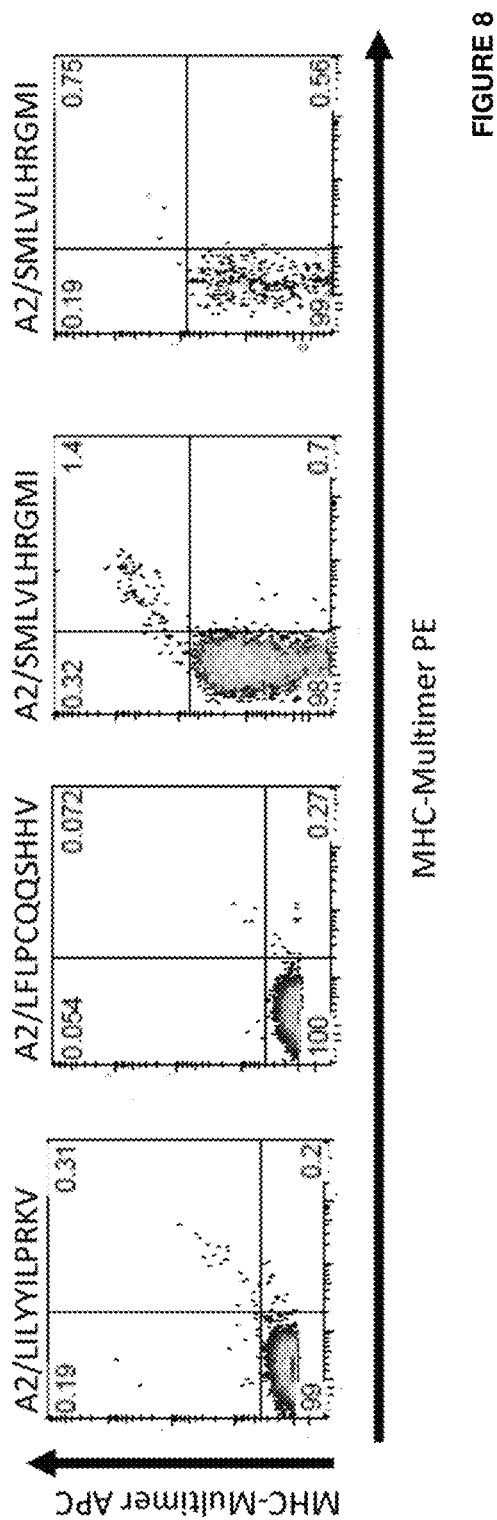

FIG. 8 depicts APC frameshift neopeptide specific T cell populations that were labeled with neopeptide-MHC multimers after 2 weeks of in vitro expansion. Double positive populations in FACS plots are specifically stained.

Figure 9:
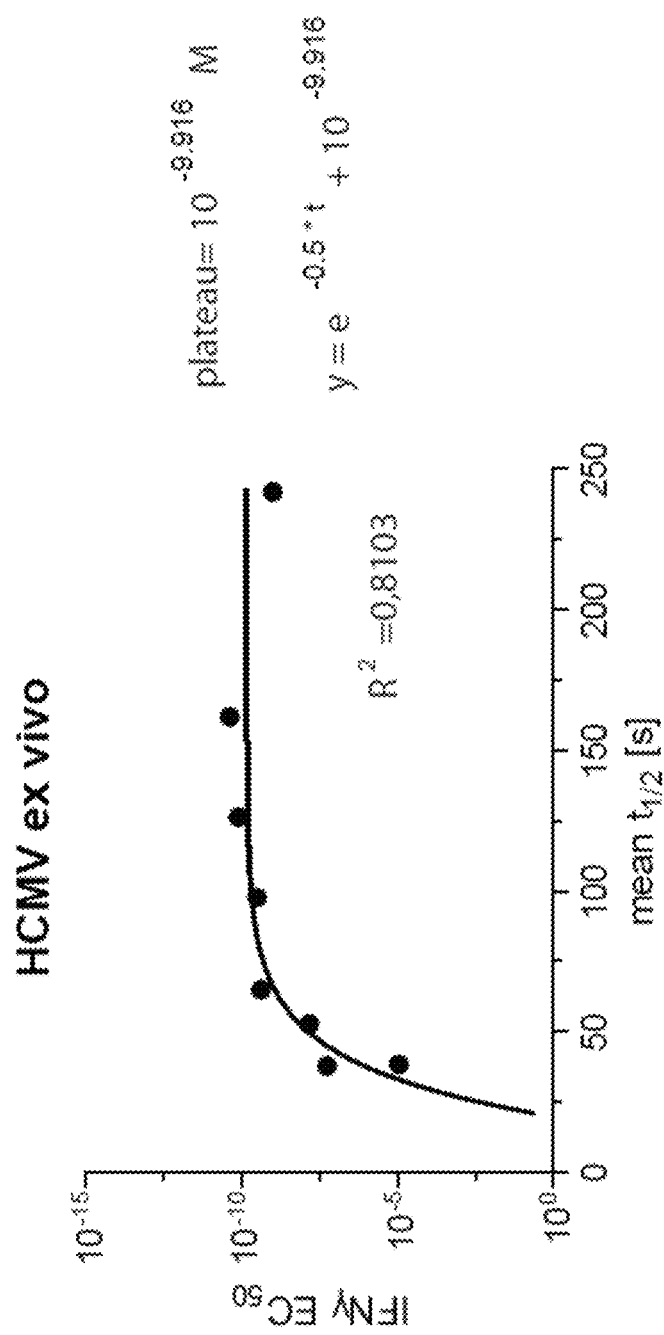

FIG. 9. Each datapoint represents the half-life-time ($t_{1/2}$) of the interaction of a Peptide-Major Histocompatibility Complex (pMHC) with a Cytomegalovirus (CMV)-specific T cell population, plotted against the concentration of the cognate peptide-epitope resulting in half-maximal IFNγ-production. In particular, T cells were contacted with MHC complexes comprising CMV-specific peptides bound thereto. T cells specific for these presented CMV-specific-peptides could then bind to the CMV-specific peptide presenting MHC complexes. The measurement of the IFNγ-production generally indicates the amount of peptide-MHC complex-stimulated lymphocytes and in this case represents the amount of T cells activated by binding to the CMV-specific peptide presenting MHC complexes.

In particular, fluorophore-coupled CMV-specific peptide MHC-monomers were used to label CMV specific T cells in the peripheral blood of chronically CMV-infected healthy human donors. CMV-specific T cells labeled with these CMV-specific peptide MHC-monomers were isolated by fluorescence activated cell sorting (FACS) ex vivo. By adding d-Biotin the StrepTactin®-backbone was displaced from the CMV-specific peptide presenting MHC complexes. The binding strength of monovalent CMV-specific peptide MHCs to their cognate TCR is generally too low to result in stable binding and thus dissociate from the cell-surface over time. The gradual release of CMV-specific peptide MHC from the surface can be observed by a decrease in fluorescence signal of CMV-specific peptide MHC. The kinetics of CMV-specific peptide MHC dissociation follows an exponential decay, which can be used to calculate a $T_{1/2}$ time that is constant throughout. The method of determining $T_{1/2}$ is further described in Nauerth M et al. (2013) "TCR-ligand $k_{off}$ rate correlates with the protective capacity of antigen-specific CD8+ T cells for adoptive transfer." Sci Transl Med. 3; 5(192):192.

Plotting the $t_{1/2}$ of CMV-specific T cell populations from different donors against the peptide concentration which stimulates the T cells to yield 50% of the maximal frequency of IFNγ-producing cells, a correlation following an exponential growth, resulting in a plateau, can be observed. With $T_{1/2}$ times below the plateau the corresponding EC50 IFNγ-values are only reached with dramatically higher peptide concentrations. Therefore the $T_{1/2}$-range can be defined between the plateau and the 50%-incline of the curve as the threshold area, below which TCRs lose their protective capacity. In particular the threshold can be seen in a $t_{1/2}$ which is higher than 50 s.

Figure 10:
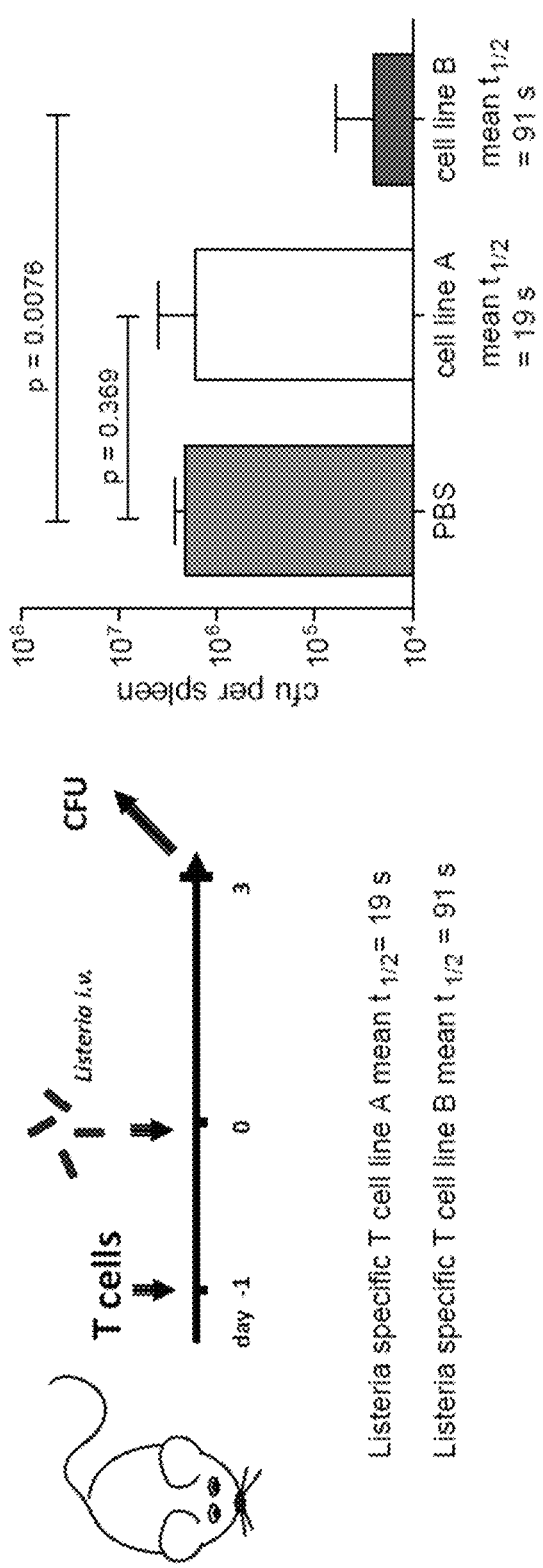

FIG. 10. T cell lines specific for an epitope of the bacterium *Listeria monocytogenes* were established by two different protocols which favor the outgrowth of either high or low avidity T cells. The avidities of the T cell lines were measured by using *Listeria*-specific peptide MHC-monomers. The $K_{off}$-rate-assay is also described detail in Nauerth M et al. (2013) "TCR-ligand $k_{off}$ rate correlates with the protective capacity of antigen-specific CD8+ T cells for adoptive transfer." Sci Transl Med. 3; 5(192):192.

The avidity of cell-line A is characterized by a $t_{1/2}$ time of 19 s. Thus, these cell lines represent a T cell line with low avidity. Cell line B shows a much slower peptide MHC dissociation of $t_{1/2}$=91 s and therefore represents a high avidity T cell line. Cell line A or B were infused into separate mice, which were infected with *Listeria* the next day. Three days after infection the bacterial load in spleens of these mice was determined. Mice, which had received cell line A, had a bacterial burden in the same range as the control mice that had not received T cells at all, whereas mice that had obtained higher avidity cell-line B demonstrated a significantly reduced bacterial burden.

This experiments shows that T cells that bind to peptide-MHC complexes with a $T_{1/2}$ of higher than 50 s indicate the presence of high avidity T cells. Such high avidity T cells have a greater potential in reducing bacterial burden. Therefore, the experiments as depicted in FIG. 5 and FIG. 6 both indicate a certain threshold of $T_{1/2}$ 50 s or higher for T cells binding to peptide specific MHCs, which allows for the selection of specifically potent T cells in general. Thus, this general concept can also be extrapolated to neopeptide-specific MHC complexes, as described herein.

FIG. 11 depicts DNA and protein sequences of the RNF43 and APC gene/protein. In addition the sequence of the β2-microglobulin is shown. The β2-microglobulin can be incorporated into the MHC molecule, preferably into an MHC class I molecule. The sequence of the β2-microglobulin comprises a signal peptide (shaded in grey), which is not incorporated in the MHC molecule (SEQ ID NO: 51) and a sequence which can become incorporated into the MHC molecule (SEQ ID NO: 52). Furthermore, the β2-microglobulin (SEQ ID NO: 52), which becomes incorporated into the MHC complex can be mutated at position 67 (shaded in grey in FIG. 11).

FIG. 12 depicts examples of promising neo-epitope candidates. 35 theoretically possible RNF43 neo-epitopes were predicted to have an MHC affinity of <20 nM using NetMHC 4.0 (Lundegaard et al. Nucleic Acids Research 2008, 36(Web Server issue):W509-12). Shown are seven examples for which multiple of the respective mutations have been described in the literature and which are all processed in an in vitro proteasome digestion assay.

DETAILED DESCRIPTION

The present invention is based on using neopeptides, which are derived from a mutation in a tumor suppressor gene and are therefore tumor-specific. These neopeptides can be used to isolate neopeptide-specific T cells. These T cells can in turn be used for autologous T cell therapy. For example, T cells can be isolated from patient biopsy specimens or blood and then be selected for tumor-specific (neopeptide-specific) T cells ex vivo. These cancer-specific T cells can then be expanded and/or reintroduced to the patient. This has been done e.g. in a study reported by Kono et al. and Rosenberg et al. (1988 and 2011), (Kono K., et al. "Prognostic significance of adoptive immunotherapy with tumor-associated lymphocytes in patients with advanced gastric cancer: a randomized trial". Clin. Cancer Res. 2002; 8:1767-1771; Rosenberg, S. A., et al., (1988) "Use of tumor-infiltrating lymphocytes and interleukin-2 in the immunotherapy of patients with metastatic melanoma. A preliminary report." N Engl J Med, 319(25): p. 1676-80; Rosenberg, S. A., et al., (2011) "Durable complete responses in heavily pretreated patients with metastatic melanoma using T-cell transfer immunotherapy." Clin Cancer Res. 17(13): p. 4550-7.) In these studies of administration of tumor-associated lymphocytes (TALs) or tumor infiltrating lymphocytes (TILs) in patients with cancer could prolong survival of patients. Notably, these studies did not specifically provide for neopeptide-specific T cells.

However, further publications did demonstrate that cytolytic T lymphocytes in cancer patients can also comprise neo-epitope specific T cells, such as CD4+ T cells (Wolfel, T., et al., (1995) "A p16INK4a-insensitive CDK4 mutant targeted by cytolytic T lymphocytes in a human melanoma." Science, 269(5228): p. 1281-4; Tran, E., et al., (2014) "Cancer immunotherapy based on mutation-specific CD4+ T cells in a patient with epithelial cancer." Science, 344 (6184): p. 641-5). This finding is also supported by a recent publication of Linnemann et al. (2014), which provides evidence for CD4+ T cells comprising neoepitope-specific TCRs (Linnemann, C., et al., (2015) "High-throughput epitope discovery reveals frequent recognition of neo-antigens by CD4+ T cells in human melanoma." Nat Med, 21(1): p. 81-5).

Identified neopeptide-specific T cells can thus be used to analyze neopeptide-specific TCRs, which can then be used for allogeneic/autologous T cell therapy. This means, that again autologous or allogenic T cells can be modified such that they recombinantly express these neopeptide-specific TCRs. These modified T cells can then be administered to the patients.

In accordance with the above, also TCRs specific to MHC-epitopes from tumor associated auto-antigens have already been used in clinical trials (Morgan, R. A., et al., (2006) "Cancer regression in patients after transfer of genetically engineered lymphocytes." Science, 314(5796): p. 126-9.). Although some therapeutic efficacy was found targeting such antigens, it has turned out very difficult to identify TCRs against tumor associated auto-antigens that demonstrate a sufficiently strong binding to elicit optimal T cell activation.

For this reason TCRs have been protein engineered to obtain higher avidities. Such engineered TCRs could elicit stronger anti-tumor responses in clinical trials (Robbins, P. F., et al., (2011) "Tumor regression in patients with metastatic synovial cell sarcoma and melanoma using genetically engineered lymphocytes reactive with NY-ESO-1." J Clin Oncol, 29(7): p. 917-24). Negative selection of auto-antigen recognizing TCRs in the thymus is believed to be the underlying mechanism restricting T cells to avidities below a certain threshold. However, it has been surprisingly found in the present invention that this threshold does not exist for T cells against neo-epitopes. Rather, as found in the present invention, the resulting range of avidities is similar as for non-self-antigens e.g. antigens coming from viral infections like CMV.

The inventors have thus surprisingly found here, that T cell therapy can be further improved by the inventive method of providing a neopeptide-specific T cell (and T cells obtainable by such method), wherein the neopeptide-specific T cell forms a complex having a half-life ($T_{1/2}$) of at least 50 s or more with a neopeptide-MHC monomer. The rationale of selecting the threshold of a half-life of 50 s or more is also explained in the Examples 1 and 2, where it has been found that such the half-life of 50 s or more for the formation of a complete of neopeptide-specific T cell with a neopeptide-MHC monomer provide therapeutically effective T cells whereas a value below this half-life results in T cells having no substantial therapeutic effect. This is particularly from Example 1 and FIG. 9, in which the half-life-time ($T_{1/2}$) of the interaction of a Peptide-Major Histocompatibility Complex (pMHC) with a Cytomegalovirus (CMV) specific T cell population is plotted against the concentration of the cognate peptide-epitope resulting in half-maximal IFNγ-production. The T cells used in this Example were obtained from the peripheral blood of chronically CMV-infected individuals. CMV-specific T cells were then isolated by MHC complexes presenting CMV-specific peptides by fluorescence activated cell sorting (FACS) ex vivo. Afterwards, the isolated T cells were stimulated with a CMV-specific peptide. Upon activation T cells release IFN-γ. In FIG. 9 the $T_{1/2}$ time of CMV-specific T cell populations from different donors was blotted against the peptide concentration which stimulations the T cells to yield 50% of the maximal frequency of IFNγ-producing cells. FIG. 9 clearly shows a correlation which follows an initial exponential increase, which results in a plateau. $T_{1/2}$ times below the plateau the corresponding EC50 IFNγ-values are only reached with dramatically higher peptide concentrations. This means that T cells with a $T_{1/2}$ of 50 s or more need much lesser peptide concentrations to be stimulated than T cells with a $T_{1/2}$ of less than 50 s ($T_{1/2}$ was determined with the method utilizing MHC-monomers as described in Nauerth et al. (2013) "TCR-ligand koff rate correlates with the protective capacity of antigen-specific CD8+ T cells for adoptive transfer." Sci Transl Med; 5(192):192ra87). Therefore the $T_{1/2}$-range between the plateau and the 50%-incline of the curve can be defined as the threshold area, below which TCRs lose their protective capacity.

Example 2 and FIG. 10 further demonstrate that this threshold value is not arbitrarily selected but rather provides for a clear functional difference. In Example 2 and FIG. 10, T cell lines specific for an epitope of the bacterium *Listeria monocytogenes* were established by two different protocols which favor the outgrowth of either high or low avidity T cells. The avidity of cell-line A is characterized by a $T_{1/2}$ time of 19 s, which is a $T_{1/2}$ below the threshold of 50 s. On the contrary, cell-line B shows a much slower pMHC dissociation of $t_{1/2}$=91 s, which represents a $T_{1/2}$ over the threshold of 50 s. Notably, $T_{1/2}$ was again determined with the method utilizing MHC-monomers as described in Nauerth et al. (2013) "TCR-ligand koff rate correlates with the protective capacity of antigen-specific CD8+ T cells for adoptive transfer." Sci Transl Med; 5(192):192ra87. Cell line A or B were then infused into separate mice, which were infected with *Listeria* the next day. Three days after infection the bacterial load in their spleens were determined. Mice, which had received cell line A had a bacterial burden in the same range as the control mice that had not received T cells at all, whereas mice that had obtained higher avidity cell-line B demonstrated a significantly reduced bacterial burden. Thus, T cells forming a complex having a half-life ($T_{1/2}$) of at least 50 s with a MHC monomer are effective in reducing bacterial burden, while T cells forming a complex having a half-life ($T_{1/2}$) of lower than 50 s with a MHC monomer are not effective.

The described Examples both indicate that there exists a certain threshold of the $T_{1/2}$ of T cells forming a complex with a MHC monomer that is indicative of the effectivity of a certain T cell. This has been shown for two different types of peptide specific T cells, namely CMV-specific, so virus-specific and bacterium-specific T cells. This proves the general concept that T cells, and in particular neopeptide-specific T cells, forming a complex having a $T_{1/2}$ of at least 50 s with a peptide (or neopeptide)-MHC monomer are therapeutically effective.

Therefore, the present invention relates to a method for providing a neopeptide-specific T cell, wherein the neopeptide-specific T cell forms a complex having a half-life ($T_{1/2}$) of at least 50 s with a neopeptide-MHC monomer, wherein said neopeptide is derived from a mutation in a tumor suppressor gene, the method comprising:
d) contacting T cells with a detectably labeled neopeptide-MHC complex;
e) isolating a T-cell, which comprises a T cell receptor (TCR) that specifically binds to the neopeptide-MHC complex; and
c) determining the $T_{1/2}$ by measuring the signal of the detectable label comprised in the MHC monomer over a period of time.

The neopeptide-MHC monomer as well as the neopeptide-MHC complex can both individually carry a detectable label. It is noted here that the neopeptide-MHC monomer used in step c) and the neopeptide-MHC complex used in step a) can carry the same detectable label. However, since steps a) and c) are carried out independently from each other the neopeptide-MHC monomer of step c) and the neopeptide-MHC complex of step a) can also carry different detectable labels. A detectable label suitable for both steps a) and c) can be any label that can be detected by standard means and methods known to the skilled artesian. In principle, the detectable label can be attached anywhere to the MHC monomer of step c) or the neopeptide MHC-complex of step a). The label can be directly fused or conjugated to the MHC monomer or MHC complex as described herein. Preferably, the label does not negatively affect the characteristics of the T cells to be stained or isolated. Examples of suitable labels are fluorescent labels, magnetic labels, chromophoric labels, spin labels suitable for electron spin resonance/electron paramagnetic resonance (EPR), or radioactive labels. The detectable label can, for example, also be an enzyme label, a luminescent label or a fluorescent label.

Examples of fluorescent labels that can be used in the present invention include phycoerythrin, allophycocyanin, coumarin, cyanine, fluorescein or rhodamine. The fluorescent label can also be an Alexa Fluor, Dylight fluor, ATTO Dye, BODIPY Dye, SETA Dye or a SeTau Dye. In one illustrative embodiment, the fluorescent label is Atto565 while in another illustrative embodiment the fluorescent label in Alexa488.

Chemiluminescent molecules that can be exploited as labels include luminol, isoluminol, acridiniumesters, thioesters and sulfonamides, and phenanthridiniumesters. A bioluminescent label can, for example, be firefly luciferase.

Alternatively, the label may be an indirect label, i.e. a label which is bound to a further reagent which in turn is capable of binding to one of the members of the multivalent binding complex as specified herein. Such a label may be added before, during or after the multivalent binding complex has been formed. An example for such a label is e.g. the enzyme label. An enzyme can be coupled to the peptide MHC complexes/monomers and visualized by the addition of a substrate for the respective enzyme. Exemplary enzyme labels include formylglycine generating enzyme, sialyltransferases, phosphopantetheinyltransferases, O-GlcNAc post-translational modification, sortagging, transglutaminase, farnesyltransferase, biotin ligase, lipoic acid ligase, N-myristoyltransferase, horseradish peroxidase (HRP), alkaline phosphatase (AP) or glucose oxidase.

The neopeptide-MHC complex used in the present invention can be any complex formed between a neopeptide and a MHC. For example, the neopeptide-MHC complex can be a neopeptide-MHC monomer or a neopeptide-MHC multimer. A neopeptide-MHC monomer comprises one MHC molecule of MHC class I or II and a neopeptide bound thereto. Correspondingly, the MHC multimer comprises more than one MHC molecule of MHC class I or II with a neopeptide bound to each of the MHC molecules. Exemplary MHC multimers include MHC tetramers, MHC pentamers or a MHC dextramers. The MHC multimer can also be a MHC dimer.

In general an MHC molecule as described herein can also comprise a β2-microglobulin. The β2-microglobulin can be of SEQ ID NO: 52 as depicted in FIG. 11. This sequence corresponds to the sequence as shown for Uniprot number: P61769 without the 20 amino acid long signal peptide as depicted in SEQ ID NO: 52 in FIG. 11. The β2-microglobulin can be further mutated at position 67 of the amino acid sequence SEQ ID NO: 52. For example, the tyrosine present at this position can be exchanged by a cysteine. This modification also allows for e.g. dye conjugation to the cysteine of this protein and subsequently the attached MHC monomer/complex. The MHC monomer and/or complex can also be truncated at the transmembrane region.

The method of the present invention can be used to isolate neopeptide-specific T cells, which are naturally occurring in a subject. It is however also within the scope of the present invention that the neopeptide-specific T cell receptors (TCRs) of the (so) obtained neopeptide-specific T cells are analyzed such that also their nucleotide and polypeptide sequence is obtained. The "T cell receptor" or "TCR" is expressed on the surface of T cells. The TCR is a disulfide-linked membrane-anchored heterodimer normally consisting of the highly variable alpha (α) and beta (β) chains expressed as part of a complex with the invariant CD3 chain molecules. The TCR is responsible for recognizing peptides such as e.g. in the present case neopeptides bound to major histocompatibility complex (MHC) molecules. The TCR is composed of two different protein chains. Most T cells consist of an alpha (α) and beta (β) chain. The TCR alpha chain is generated by VJ recombination, whereas the beta chain is generated by VDJ recombination.

The variable domain of both, the TCR α-chain and β-chain, each have three hypervariable or complementarity determining regions (CDRs) that normally contact the peptide/neopeptide. The CDR3 is the main CDR responsible for recognizing to interact with the N-terminal part of the peptide/neopeptide, whereas CDR1 of the β-chain interacts with the C-terminal part of the peptide/neopeptide. However, a minor part of the T cells have a TCR that consists of gamma and delta (γ/δ) chains. The generation of the TCR gamma chain involves VJ recombination, whereas generation of the TCR delta chain occurs by VDJ recombination. Therefore, the TCR can be a TCR with an alpha and a beta chain and/or a TCR with a gamma and delta chain.

It is further envisioned by the present invention that a T cell comprises a TCR that specifically binds to the neopeptide-MHC complex and/or neopeptide MHC monomer. In general, for the neopeptide-specific T cells described herein, binding can be considered specific when the binding affinity is in the range 1-100 μM ($K_D$), preferably in the range of 1-700 nM. The term "specific binding" as used herein also includes that the neopeptide-specific T cell is activated via binding to the neopeptide-MHC complex.

Characteristics of a T-cell activation as used herein are known to the skilled artesian and for example described in Smith-Garvin et al., (2009) "T cell activation" Annu Rev Immunol. 2009; 27:591-619. For example, T cell activation can lead to a number of immune responses such as activation of phagocytic cells and direct cell killing by e.g. the activated T cell. An activated T cell can also release different cytokines such as IFN-γ.

With the knowledge of the neopeptide-specific TCR polypeptide and/or coding nucleotide sequences neopeptide-specific T cells can then be produced recombinantly. Therefore, the method of the present invention can further comprise that step b) further comprises
b.1) isolating the neopeptide-specific TCR;
b.2) determining the TCR α chain and β chain sequences;
b.3) recombinantly expressing the neopeptide-specific TCR in a T cell.

It is also envisioned by the present invention that in step b.2) instead of the alpha and beta chain, the TCR gamma and delta chain sequences are determined and subsequently expressed in step b.3).

The method of the present invention provides for a neopeptide-specific T cell, either directly obtained from a subject or recombinantly produced as described herein that forms a complex having a half-life ($T_{1/2}$) of at least 50 s with a neopeptide-MHC monomer. In this context, it is noted that the formation of complex (C) between a neopeptide-MHC monomer (L) and neopeptide-specific T cell (P) can be described by a two-state process noted $$C \rightleftharpoons P+L$$

The corresponding dissociation $K_d$ constant is defined as $$K_d = \frac{[P][L]}{[C]}$$

wherein [P], [L], and [C] are the equilibrium molar concentrations of the neopeptide-specific T cell (P), the neopeptide-MHC monomer (L) and the respective complex at a given temperature and pressure. The dissociation $K_d$ constant can also be expressed as the ratio of the constant of the on-rate ($k_{on}$) for the speed of association/formation (also called association rate constant) of the complex and the constant of the off-rate ($k_{off}$) for the dissociation of the complex (also called dissociation rate constant) with $$K_d = k_{off}/k_{on}$$

In the present application, the values of the thermodynamic and kinetic constants $K_d$, $K_a$, $k_{on}$ and $k_{off}$ refer to their determination under "standard conditions", i.e. a temperature of 4° C. and atmospheric pressure of 1.013 bar.

In the present invention, it has been found, as mentioned above, that the $k_{off}$ rate [s$^{-1}$] for the binding of the neopeptide-specific T cell to the neopeptide-MHC monomer is the determinant for the efficiency of the neopeptide-specific T cell to e.g. overt target cell killing. In particular a half-life of more than 50 s has been shown to be an indicator of the efficiency of the neopeptide-specific T cells.

It is noted in this context that the half-life $T_{1/2}$ of the complex (C) between the neopeptide-MHC monomer (L) and the neopeptide-specific T cell (P) can be expressed as $\ln2/k_{off}=0.693/k_{off}$. Thus, with a $k_{off}$ of $1.0\times10^{-4}$ sec$^{-1}$, it takes 6390 seconds to reduce the concentration of the complex between the neopeptide-MHC monomer and the neopeptide-specific T cell by half, assuming that the dilution is sufficient that rebinding of the dissociated receptor binding reagent to the receptor molecule can be neglected.

In principle, the determination of the $T_{1/2}$ can be performed by means and methods known to the person skilled in the art. For example, the $k_{off}$-rate for the binding of the neopeptide-MHC monomer to the neopeptide-specific T cell and, of course, also the $k_{on}$ rate can be determined via standard methods, such as surface plasmon resonance (SPR), for example, using the BIAcore technology (SPR; Jonsson, U. et al. (1991) Biotechniques, 11, 620-627). This determination is within the average knowledge of the person skilled in the art. Usually, the determination is carried out at 25° C. by surface plasmon resonance analysis, at a suitable concentration of neopeptide-MHC monomer with the neopeptide-specific T cell being immobilized on the surface of a respective sensor chip. The neopeptide-MHC monomer is applied on the chip in different concentrations (usually around the estimated $K_d$ value as determined from preliminary characterizations), using flow rates in the range of μl/min.

Another possibility to obtain the $T_{1/2}$ is to carry out neopeptide-MHC monomer dissociation experiments. Such dissociation experiments can be based on a reversible staining method. A reversible staining method can include a multivalent binding complex formation (multimerization) between e.g. a streptavidin-mutein and a neopeptide-MHC monomer comprising e.g. a streptavidin binding peptide. One multimerization reagent that comprises at least one or two binding sites for a streptavidin binding peptide is a streptavidin mutein (e.g. "Strep-Tactin®"). In this way a neopeptide-specific MHC monomer that binds to neopeptide-specific T cell can be reversibly multimerized by e.g. Strep-tag®/Strep-Tactin® complex formation (see also FIG. 1.) This method of determining $k_{off}$ rates of peptide MHC complexes from peptide specific TCRs is known in the art and further described in Nauerth M et al. (2013) "TCR-ligand koff rate correlates with the protective capacity of antigen-specific CD8+ T cells for adoptive transfer." Sci Transl Med. 3; 5(192):192.

Considering the above, the determination of the $T_{1/2}$ can be performed with a neopeptide-MHC monomer that further comprises a streptavidin binding peptide. It is however also envisioned that a neopeptide-MHC complex comprises a streptavidin binding peptide. The streptavidin binding peptide is capable of binding to a streptavidin mutein.

Exemplary streptavidin binding peptides can comprises a sequence selected from Trp-Ser-His-Pro-Gln-Phe-Glu-Lys (SEQ ID NO: 47, also known as Strep-tag®), Trp-Arg-His-Pro-Gln-Phe-Gly-Gly (SEQ ID NO 46, also known as Strep-tag® II), Trp-Ser-His-Pro-Gln-Phe-Glu-Lys-(GlyGlySer)$_3$-Trp-Ser-His-Pro-Gln-Phe-Glu-Lys (SEQ ID NO: 48), Trp-Ser-His-Pro-Gln-Phe-Glu-Lys-(GlyGlyGlySer)$_2$-Trp-Ser-His-Pro-Gln-Phe-Glu-Lys (SEQ ID NO: 49) or Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 50). The streptavidin binding peptide can comprise the sequence Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys that is also known as Twin-Strep-tag® (SEQ ID NO: 50). These streptavidin binding peptides are known and, described, for example, in U.S. Pat. No. 7,981,632, International Patent Application WO 02/077018 and International Patent Application WO 2014/076277.

Furthermore, the streptavidin binding peptide can be directly fused to the neopeptide-MHC monomer/complex or conjugated via a linker to the neopeptide-MHC monomer/complex. The same applies to the detectable label that is carried by the neopeptide-specific complex/monomer. Also this detectable label can be directly fused to or be conjugated via a linker to the neopeptide-specific MHC monomer/complex.

Suitable linkers can in principle be attached to the streptavidin binding peptide or neopeptide-specific complex/monomer at any suitable position. Suitable linkers are known in the art and, for example, described in Chen et al. (2013) "Fusion protein linkers: property, design and functionality" Adv Drug Deliv Rev; 65(10):1357-69. The linker can therefore be any linker known in the art. Preferably, the linker does not interfere with the function of the streptavidin binding peptide or MHC complex/monomer.

The linker may, for example, be a straight or branched hydrocarbon based moiety that is coupled to the both partners via activated chain side groups such as amino, thiol or hydroxyl groups. The linker can also comprise cyclic moieties. If the linking moiety is a hydrocarbon-based moiety the main chain of the linker may comprise only carbon atoms but can also contain heteroatoms such as oxygen (O), nitrogen (N) or sulfur (S) atoms. The linker may for example include a $C_1$-$C_{20}$ carbon atom chain or a polyether based chain such as polyethylene glycol based chain with —(O—CH$_2$—CH$_2$)— repeating units. In typical embodiments of hydrocarbon based linkers, the linking moiety may comprise between 1 to about 150, 1 to about 100, 1 to about 75, 1 to about 50, or 1 to about 40, or 1 to about 30, or 1 to about 20, including 2, 3, 4, 5, 6, 7, 8, 9, 10, 11, 12, 13, 14, 15, 16, 17, 18, and 19 main chain atoms.

The linker may however also be a peptide linker of any suitable length as long as the linker does not interfere with the function of the streptavidin binding peptide or MHC complex/monomer. The linker may comprises two or more, five or more, 10 or more, 15 or more, or 20 or more amino acid residues. The peptide linker may comprise any amino acid residue. The peptide linker may be rich in small or polar amino acids such as Gly and Ser, but can contain additional amino acids such as Thr and Ala to maintain flexibility, as well as polar amino acids such as Lys and Glu to improve solubility.

It is also envisioned by the present invention that a cysteine on a "glycine-serine" linker is inserted between the neopeptide-MHC complex and/or neopeptide-MHC monomer and the streptavidin binding peptide. Therefore the neopeptide-MHC complex and/or neopeptide-MHC monomer can comprise a linker of the sequence C-G-S. In the case of the neopeptide-MHC complex and/or neopeptide-MHC monomer the detectable label may be conjugated or fused N- or C-terminally to the protein. It is also envisioned by the present invention that the detectable label is conjugated C-terminally to the neopeptide-MHC complex and/or neopeptide-MHC monomer. The MHC monomer/complex loaded with neopeptide can for example be linked to a Strep-tag III region, which is either conjugated to the fluorescent dye such as Atto565 over a maleimide reaction with a cysteine on a G-S linker at the C-term.

As described, the neopeptide-MHC monomer/complex may also be constructed such that it reversibly binds to a streptavidin mutein. Suitable streptavidin muteins that can be used for the reversible staining, include the streptavidin muteins "1" and "2" that are known from U.S. Pat. No. 6,103,493 or European Patent 0 835 934 and are commercially available from IBA GmbH under the trademark "Strep-Tactin®". Other suitable streptavidin muteins are described in International Patent Application WO 2014/076277.

Therefore, step c) of the method of the present invention can further comprise contacting the neopeptide-MHC monomer with a streptavidin mutein. More particularly, step c) can comprise c.1) contacting T cells with the neopeptide-MHC monomer and a streptavidin mutein, wherein the neopeptide-MHC monomer comprises a streptavidin binding peptide that reversibly binds to the Streptavidin mutein.

In order to cause the dissociation between a neopeptide-specific MHC monomer/complex (comprising the streptavidin binding peptide) and the streptavidin mutein, a molecule (ligand) which binds with higher affinity to the streptavidin mutein than the streptavidin binding peptide can be added. Such a molecule can, for example, be D-biotin. Therefore, the method of the present invention can further comprise step c) further comprising c.2) adding D-biotin.

Since D-biotin can trigger the dissociation between a streptavidin binding peptide and the streptavidin mutein, the method of the present invention can include that the determination of $T_{1/2}$ is performed after the addition of D-biotin.

Thus, the present invention can also relate to a method for providing a neopeptide-specific T cell, wherein the neopeptide-specific T cell forms a complex having a half-life ($T_{1/2}$) of at least 50 s with a neopeptide-MHC monomer, wherein said neopeptide is expressed by a tumor suppressor gene, the method comprising:

a) contacting T cells with a detectably labeled neopeptide-MHC complex;
b) isolating a T-cell, which comprises a T cell receptor (TCR) that specifically binds to the neopeptide-MHC complex; and
c.1) contacting T cells with the neopeptide-MHC monomer and a streptavidin mutein, wherein the neopeptide-MHC monomer comprises a streptavidin binding peptide that reversibly binds to the Streptavidin mutein;
c.2) adding D-biotin.
c.3) determining the $T_{1/2}$ by measuring the signal of the detectable label comprised in the MHC monomer over a period of time.

In the method of the present invention the detectable label is measured over a period of time. In principle, what is measured is the decay or disappearance of the detectable label over time. Therefore, the maximal intensity of the detectable label indicates the starting point of the dissociation of MHC monomers. The label decays or disappears due to the dissociation of the neopeptide-specific monomer/complex from the neopeptide-specific T cell. It is envisioned by the present invention that the signal intensities of the detectable label are blotted over a period of time while the $k_{off}$ rate and $T_{1/2}$ are calculated. The period of time, in which the measurement of the decay or disappearance of the detectable label can be any time that is necessary to observe the dissociation. For example, the period of time can be started before the addition of D-biotin or after the addition of biotin. As such the period of time over which the signal is measured in step c) can be a period of 800 s or less, 750 s or less, 700 s or less, 650 s of less, 600 s or less, 500 s or less, 400 s or less, 300 s or less or 200 s or less. It can also be a period of 190 s, 180 s, 170 s, 160 s, 150 s, 140 s, 130 s, 120 s, 110 s, 100 s, 90 s, 80 s, 70 s, 60 s or 55 s. The measurement can for example take place every 20 s, 18 s, 15 s, 13 s, 10 s, 9 s, 8 s, 7 s, 6 s, 5 s, 4 s, 3 s, 2 s or 1 s after the addition of D-biotin. The measurement can thus also take place every 10 s after the addition of D-biotin. The measurement can, however, also be started shortly before the addition of biotin.

The period of time which detects the decay or disappearance of the detectable label over time should be long enough to observe the $T_{1/2}$ of the complex between the neopeptide-specific T cell and the neopeptide-MHC monomer. The $T_{1/2}$ of this complex can be at least 55 s or more, 60 s or more, 65 s or more, 70 s or more, 75 s or more, 80 s or more, 85 s or more, 90 s or more, 95 s or more, 100 s or more, 105 s or more or 110 s or more. It can also be 115 s, 120 s, 125 s, 130 s 135 s or 140 s or more.

It is further contemplated by the present invention that the measurement of $T_{1/2}$ can be performed at about 4° C. Thus, step c) of the method of the present invention can be performed at about 4° C. It is however also envisioned that neopeptide-specific T cells bound via the streptavidin binding peptide of the neopeptide-specific MHC complex/monomer to the streptavidin mutein are kept at 4° C. In principle, however, the whole method of the present invention can be performed at any temperature. Such a temperature may be any temperature below 25° C., 20° C., 15° C., 10° C., 9° C., 8° C., 7° C., 6° C. or 5° C.

The measurement of $T_{1/2}$ is performed by measuring the decay or disappearance of the detectable label as described herein. Particularly suited are therefore fluorescent dyes for the purposes of the present invention. Therefore, the detectable label can be a fluorescent dye, preferably Atto565.

As known to the skilled artesian one observation with fluorescent dyes is that fluorescent signals are also lost due to photo bleaching. Therefore, the method of the present invention also contemplates that the measured signal of the fluorescent dye is corrected for photo bleaching. In principle any method known in the art for correcting for photo bleaching is contemplated by the present invention. One method for the correction of photo bleaching is described in detail in Supplementary Method 1 of Nauerth et al., (2013) "TCR-ligand $k_{off}$-rate predicts protective capacity of antigen-specific CD8+ T cells for adoptive transfer." Sci Transl Med.; 5(192): 192. In short, an effective dissociation probability k, which is actually observed when performing the $k_{off}$-rate experiment can be obtained by the following formula (10). The grade of bleaching has to be quantified beforehand in dedicated measurements obtaining $k_{bleach}$. The photo bleaching rate can for example be determined by monitoring and analyzing Strep-Tactin® coated beads multimerized with detectably labeled conjugated MHC-molecules with identical settings as used for the $k_{off}$ rate measurements. The term $T_{1/2}$ is equally obtained by performing experiments.

$$k = k_{off} + k_{bleach} \Leftrightarrow \frac{1}{t} = \frac{1}{t_{1/2}} + \frac{1}{t_{bleach1/2}} \quad (10)$$

Thus, the method of the present invention comprises in principle two important steps. First, a neopeptide-specific T cell has to be obtained. In a second step then the $T_{1/2}$ of the neopeptide-specific T cell and the neopeptide-MHC monomer is determined. Notably, the method of the present invention further envisions that the isolated neoepitope-specific T cell obtained in step b) is expanded. In this way, for example, a part of these expanded T cells can be utilized for TCR sequence analysis, while the other part of these expanded T cells serves for $k_{off}$ rate determination. Therefore, it is also envisioned that neopeptide-specific T cells are expanded on a clonal (single cell) basis.

As described herein neopeptide-specific T cells can be obtained either directly from a subject but they can also be produced recombinantly. For the recombinant production of T cells it is necessary to identify/determine TCR gamma and delta (γ/δ) chains or TCR α chain and β chain sequences, which TCR binds to the neopeptide presenting MHC monomer/complex. There are different methods known in the art for determining specific TCR sequences. The identification and isolation of neo-peptide specific T-cells can for example be carried out as described in Anderson et al. "Parallel detection of antigen-specific T cell responses by combinatorial encoding of MHC multimers", Nature Protocols Vol 7 No. 5, 2012, pages 891 to 902, as described in Hadrup et al. "Parallel detection of antigen-specific T-cell responses by multidimensional encoding of MHC multimers" Nature Methods Vol. 6, No. 7, 2009, pages 520 to 528, in Dössinger et al. (2013) "MHC multimer-guided and cell culture-independent isolation of functional T cell receptors from single cells facilitates TCR identification for immunotherapy." PLoS One; 8(4):e61384 or as described in Linnemann, C., et al., "High-throughput epitope discovery reveals frequent recognition of neo-antigens by CD4+ T cells in human melanoma". Nat Med, 2015. 21(1): pages 81 to 85.

Single neopeptide-specific T cells, which have been isolated by neopeptide-specific MHC monomer/complex, for example, using the methodology described by Dössinger et al (2013), supra or Linnemann et al, (2015), supra, can subsequently be sequenced. This approach may be technically challenging since simultaneous extraction of both TCR chains can be difficult. Therefore, such single cell based TCR sequencing techniques that can be used in the present invention, may additionally make use of sets of degenerate primers binding to consensus motifs or rapid amplification of cDNA ends (RACE) PCR. Such techniques are, for example, described in Ozawa et al. (2008) "Comprehensive analysis of the functional TCR repertoire at the single-cell level." Biochem Biophys Res Commun. 367(4):820-5 and Sun et al. (2012) "Unbiased analysis of TCRα/β chains at the single-cell level in human CD8+ T-cell subsets." PLoS One.7(7):e40386. Thus, the isolating of the neoepitope-specific TCR can be performed by PCR.

It is, however, also envisioned by the present invention that the PCR for isolating the neopeptide specific TCR sequences comprises
a) a gene-specific reverse transcription;
b) an anchor PCR; and
c) a nested PCR.

This method of TCR sequencing has also been described in detail in Stemberger et al. (2014) "Lowest numbers of primary CD8(+) T cells can reconstitute protective immunity upon adoptive immunotherapy." Blood 124(4):628-37. The gene-specific reverse transcription is known to the skilled artesian. Therefore, the present invention contemplates any method known to the skilled artesian for gene-specific reverse transcription. Such a gene-specific reverse transcription results in cDNA transcripts. This method step can be performed at 40° C. to 80° C. for a period of time. Reverse transcription can be performed at a temperature of 45° C., 46° C., 47° C., 48° C., 49° C., 50° C., 51° C., 52° C., 53° C., 54° C., 55° C., 65° C., 66° C., 67° C., 68° C., 69° C., 70° C., 71° C., 72° C., 73° C., 74° C. or 75° C. The period of time for reverse transcription can be 5 minutes, 10 minutes, 15 minutes, 20 minutes, 25 minutes, 30 minutes, 35 minutes, 40 minutes or 45 minutes. It is also envisioned that reverse transcription is performed at a temperature of 51° C. for 20 minutes followed by a temperature of 70° C. for 30 minutes.

The product obtained by gene-specific reverse transcription can then be treated such that excess single-stranded primer oligonucleotides are degraded. Techniques for reducing excess single-stranded primer oligonucleotides are known to skilled artesian. Any known technique provide for reducing excess single-stranded primer oligonucleotides are therefore envisioned by the present invention. For example, gene specific reverse transcription can be followed by a primer exonuclease digestion by the addition of exonuclease-I. Exonuclease-I digestion can be performed at 37° C. for 30 minutes.

It is further contemplated by the present invention that a set of three gene-specific reverse transcription primers is used for each TCR sequence, so three primers for each of α, β, γ or δ sequence.

It is further envisioned by the present invention that the PCR for isolating the neopeptide-specific TCR sequences comprises an anchor PCR. For the purposes of the method of the present invention such an anchor PCR refers to the enzymatic addition of nucleotides either to the 3' or 5' end of the cDNA transcripts obtained via gene-specific reverse transcription. The rationale behind the addition of nucleotides is to generate an artificial binding site upstream of the unknown V-segment sequence of the TCR. In principle any sequence can be added to the cDNA. For example, an oligo-dG stretch can be added to the 3' end of the cDNA transcripts. An oligo-dG stretch may comprise the sequence GGGGG (SEQ ID NO: 53). Therefore, the method also contemplates that the anchor PCR results in an oligo-dG stretch at the 3' end of the cDNA.

It is further envisioned by the present invention that the artificial binding site that has been generated by the enzymatic addition of nucleotides to cDNA transcripts is further prolonged by an additional PCR step. In particular, for such an elongation of the sequence a primer is utilized that binds to the added sequence and has an overhang. The term "primer" as described herein refers to an oligonucleotide that serves as a starting point for DNA synthesis. In e.g. PCR methods, primers are used to determine the DNA or cDNA fragment to be amplified by the PCR process. Usually, they need to match the beginning and the end of the DNA fragment to be amplified. The length of primers is usually not more than 10, 20, or 30 nucleotides and usually 18-24 nucleotides. Primers can be designed that have additional "overhang" sequence at the 3' ends that will subsequently be incorporated into the PCR product. For the incorporation of such an overhang to the cDNA product a first cycle of the PCR program causes the primers to anneal to the template at the complementary sites on the primers and create a product that contains the desired overhang regions. Subsequent cycles then amplify this strand of DNA to give a pool of PCR product that contains the prolonged cDNA sequence.

For example, the primer as used for the anchor PCR can bind to the oligo-dG stretch. Such a primer can have an overhang of 5, 10, 15, 20, 25, 30, 35, 40, 45, 50, 55, 60, 65, 70 or 80 nucleotides or more. In addition, such a primer can be modified such that it carries a phosphorothioate at its 3' terminus. The phosphorothioate can prevent/decrease an exonucleolytic attack on primer molecules, usually observed due to 3' to 5' exonuclease activities.

To obtain TCR sequences finally a nested PCR can be performed. Nested polymerase chain reaction involves two sets of primers, used in two successive runs of polymerase chain reaction, the second set intended to amplify a secondary target within the first run product. It is envisioned by the present invention that nested PCR amplification takes place in separate reactions for the alpha and beta or for the gamma and delta TCR sequences. Thus, the method of the present invention can use the nested PCR to amplify the α and β chains of the TCR. Alternatively, the method of the present invention can use the nested PCR to amplify the γ and δ chains of the TCR.

Using the method comprising a gene-specific reverse transcription, anchor PCR and nested PCR as described herein full length TCR α sequences, β sequences or γ sequences, δ sequences can be obtained. The method of the present invention provides a method in which more than 3%, 5%, 7%, 10%, 13%, 15%, 17% 20% 25% of all cell samples result in full-length products/sequences of the TCR α, β or γ, δ chain sequences. The method of the present invention also provides a method in which more than 3%, 5%, 7%, 10%, 13%, 15%, 17% 20% 25% of all cell samples result in sequences of the variable part of the TCR α, β or γ, δ chain sequences.

As described herein, the isolation of the TCR sequences is started after isolation e.g. FACS isolation of T cells, or even single cells, which specifically bound to neopeptide presenting MHC monomers/complexes. In this context it is further contemplated by the present invention that the PCR protocol or the gene-specific reverse transcription is started within 48 hours, 36 hours or 24 hours after T cell isolation, preferably 48 hours after T cell isolation.

The obtained TCR sequences can then be introduced into any cell, to provide for a cell with a functional TCR. How such an introduction can be performed is known to the skilled artesian. For example, the TCR sequences can be retrovirally into human PBMC cells or T cells. Of course, this harbors great potential for a personalized medicine. For example it is possible, to isolate suitable cells for TCR transduction from the subject, which can then be re-introduced into the subject after successful TCR transduction.

Turning now to the neopeptide which is used to isolate neopeptide-specific T cells in the method of the present invention. The term "neopeptide" when used herein refers to a neopeptide that is derived from a mutation in (or expressed by) a tumor suppressor gene. In such neopeptides the genetic information can be altered such that it results in novel amino acid sequences. In principle, the genetic information can be altered in any way as long as novel amino acid sequences result from such alteration/s. For example, the neopeptide can be expressed by a tumor suppressor gene comprising a point mutation and/or a frameshift mutation.

A "point mutation" when used herein refers to a single-nucleotide polymorphism in which a nucleotide is replaced. However, it is also envisioned by the present invention that 2, 3, 4, or more single-nucleotide polymorphisms are present in the tumor suppressor gene. In any case, if such point mutation/s results in an altered peptide sequence after translation then a neopeptide arises. In this context it is noted that the point mutation can be a missense or a nonsense mutation.

A "frameshift mutation" when used herein refers to a type of mutation, which changes the amino acid sequence from the site of the mutation due to addition or deletion of (a number of) nucleotide(s). This causes a shift in the reading frame of the codons in the mRNA. If this shift in the reading frame leads to an alteration in the amino acid sequence at protein translation then a neopeptide results. Thus both types of alterations of the genetic sequence as described herein can then provide for novel neopeptides after translation of the DNA sequence.

The frameshift mutation can for example be the result of an insertion or deletion. The frameshift mutation can be selected from a −5, −4, −3, −2, −1, +1, +2, +3, +4 or +5 mutation. This means that the reading frame is changed by deletion of 1 to 5 amino acids (−1 to −5) or by the addition of 1 to 5 amino acids (+1 to +5). In one embodiment, the frameshift mutation is a −1 mutation. In another embodiment, the frameshift mutation is a +1 mutation. The frameshift mutation can also be a +1 or −1 mutation. However, it is also envisioned by the present invention that the frameshift mutation is a −6, −7, −8, −9, −10, −11, −12, −13, −14, −15, −16, −17, −18, −19, −20, −25, −30, −35, −40, −50, −60, −70 or −100 frameshift mutation. The present invention also encompasses +6, +7, +8, +9, +10, +11, +12, +13, +14, +15, +16, +17, +18, +19, +20, +25, +30, +35, +40, +50, +60, +70 or +100 frameshift mutations.

In addition to the structural features the neopeptide as used in the methods of the present invention the neopeptide can alternatively or additionally also provide for functional features. For example, the neopeptide can be immunogenic. The term "immunogenic" or "immunogen" as used herein means the ability of the neopeptide to induce an immune response. This immune response may be determined in vitro or ex vivo or in vivo in a subject. In general the person skilled in the art knows means and methods to analyze the immunogenic potential of a given neopeptide. In principle, an immunogen can elicit the production of both specific antibodies and specific effector T cells.

For example, the potential of a certain neopeptide to induce the production of neopeptide-specific antibodies can be analyzed as follows. This can be achieved by assaying neopeptide-specific antibody that accumulates in the fluid phase of the blood or plasma by e.g. high affinity chromatography, radioimmunoassay (RIA) and enzyme-linked immunosorbent assay (ELISA). In this way response of B cells to an injected immunogen is usually measured by analyzing the specific antibody produced in a humoral immune response.

The potential of a certain neopeptide to induce the production of specific effector T cells can be measured by e.g. the ELISPOT assay. It assays the response of T cells on the basis of cytokine production. In the ELISPOT assay, cytokine secreted by individual activated T cells is immobilized as discrete spots on a plastic plate, which are counted to give the number of activated T cells. Alternatively, measurements based on flow cytometry can detect e.g. fluorescently labeled cytokines within activated T cells. Finally, T cells can also be directly detected on the basis of the specificity of their receptor, using fluorochrome-tagged tetramers of specific MHC:peptide complexes/monomers. One way of measuring or detecting activated T cells is the analysis of IFNγ as described in Example 1.

As shown in Examples 1 and 2 also the avidity of peptide specific T cells plays an important role in the immune response. The term "avidity" when used herein describes the sum of single TCR affinities to a peptide:MHC complex/monomer, which determines the binding strength between these two components. Highly avidity T cells can bind in low concentrations to peptide-MHC molecules. On the other hand, low avidity T cells need high concentrations for binding to peptide-MHC molecules. There also exist standard protocols to isolate high avidity T cells and low avidity T cells are known to the person skilled in the art. For example, such isolations are described in Alexander-Miller, Leggatt and Berzofsky (1996) "Selective expansion of high- or low-avidity cytotoxic T lymphocytes and efficacy for adoptive immunotherapy." Proc Natl Acad Sci USA; 93(9): 4102-7. For the purposes of the present invention a high-avidity T cell forms a complex having a half-life ($T_{1/2}$) of at least 50 s, 60 s, 70 s, 80 s, 90 s, 100 s, 110 s, 120 s or 130 s with a neopeptide-MHC monomer. On the contrary, a low avidity T cells would form a complex having a half-life ($T_{1/2}$) of at most 45 s, 40 s, 35 s, 30 s, 25 s, 20 s, 15 s, or 10 s with a neopeptide-MHC monomer.

This immune response may also be reflected in ex vivo experiments of neopeptide-specific T cells by the ability of the production of IFNγ. This cytokine is e.g. released upon immunogenic stimulation of T cells.

In contrast to the immunoglobulins, which interact with pathogens and their toxic products in the extracellular spaces of the body, T cells only recognize foreign immunogens that are displayed on the surfaces of the body's own cells. These immunogens can derive from pathogens such as viruses or intracellular bacteria, which replicate within cells, or from pathogens or their products that cells have internalized by endocytosis from the extracellular fluid in the normal in vivo situation of an otherwise healthy subject not suffering from cancer.

Mature T cells can have the ability to respond to foreign, but not self, peptides bound to self MHC molecules. However, a T cell may also bind to non-self-peptide presenting MHC molecules. A T cell that is specific for one peptide: MHC combination may thus cross-react with peptides presented by other, non-self (allogeneic), MHC molecules. In this context it is noted that for a "perfect" binding of the TCR to the peptide:MHC the TCR binds to both, the peptide and MHC. Thus, the peptides bound to the allogeneic MHC molecule may fit well to the T-cell receptor (TCR), allowing binding even if there is not a good fit with the MHC molecule. Alternatively, but less often, the allogeneic MHC molecule may provide a better fit to the T-cell receptor, giving a tight binding that is thus less dependent on the peptide that is bound to the MHC molecule. Thus, a neopeptide of the present invention can also be a foreign epitope.

An "epitope" when used herein refers to a part of an immunogen that is recognized by the immune system, specifically by antibodies, B cells, or T cells. Such an epitope may have a length of 3, 5, 8, 9, 10, 11, 12, 15, 17, 20, 23, 25, 27, 30 amino acids. For HLA class I MHCs the epitope may have a length of 2, 3, 4, 5, 6, 7, 8, 9 or 10 amino acids. For HLA class II MHCs the epitope may have a length of 3, 5, 7, 9, 10, 13, 15, 17 or 20 amino acids. Although epitopes are usually non-self-proteins, sequences derived from the host that can be recognized (as in the case of autoimmune diseases) can also serve as epitopes.

Exemplary neopeptides include neopeptides which can be selected from the group consisting of any one of SEQ ID NO: 1-SEQ ID NO: 45. These neopeptides are also listed in table 1 as depicted below as well as in FIGS. 3 and 7.

TABLE 1 depicts peptide sequences of neopeptides generated from the RNF43 suppressor gene (SEQ ID NOs: 1-23) and from the APC tumor suppressor gene (SEQ ID NOs: 24-45). KD values for SEQ ID NOs: 1-23 are given for HLA-A02:01.

| SEQ ID NO: | Position or Frame position | Peptide | Kd, nM | Frame or Frame type |
|---|---|---|---|---|
| 1 | 141 | SLLPTCWAL | 7 | Deletion Frame 212-418 |
| 2 | 135 | AMPTTTSLL | 178 | Deletion Frame 212-418 |
| 3 | 142 | LLPTCWALPGV | 181 | Deletion Frame 212-418 |
| 4 | 172 | ALGITASPEL | 400 | Deletion Frame 212-418 |
| 5 | 55 | SLTSLRIEL | 101 | Deletion Frame 83-157 |
| 6 | 52 | VLSSLTSLRI | 192 | Deletion Frame 83-157 |
| 7 | 55 | SLTSLRIELL | 195 | Deletion Frame 83-157 |
| 8 | 148 | TQLARFFPI | 28 | Deletion Frame 527-699 |

TABLE 1-continued depicts peptide sequences of neopeptides generated from the RNF43
suppressor gene (SEQ ID NOs: 1-23) and from the APC tumor suppressor gene
(SEQ ID NOs: 24-45). KD values for SEQ ID NOs: 1-23 are given for HLA-A02:01.

| SEQ ID NO: | Position or Frame position | Peptide | Kd, nM | Frame or Frame type |
|---|---|---|---|---|
| 9 | 152 | RFFPITPPV | 136 | Deletion Frame 527-699 |
| 10 | 39 | WLARLGWRV | 15 | Deletion Frame 83-157 |
| 11 | 92 | SLSQPLAQL | 136 | Deletion Frame 527-699 |
| 12 | 99 | QLTPPASAPV | 241 | Deletion Frame 527-699 |
| 13 | 42 | RLGWRVSEEPV | 347 | Deletion Frame 83-157 |
| 14 | 98 | AQLTPPASAPV | 373 | Deletion Frame 527-699 |
| 15 | 100 | LTPPASAPV | 435 | Deletion Frame 527-699 |
| 16 | 71 | SMAAVLLSA | 24 | Deletion Frame 419-501 |
| 17 | 71 | SMAAVLLSAA | 68 | Deletion Frame 419-501 |
| 18 | 28 | VLDGPPAPA | 227 | Deletion Frame 83-157 |
| 19 | 66 | SAYRGSMAAV | 475 | Deletion Frame 419-501 |
| 20 | 27 | RVLDGPPAPA | 479 | Deletion Frame 83-157 |
| 21 | 91 | YISIGLAPSA | 346 | Deletion Frame 212-418 |
| 22 | 78 | ASMSSIVTV | 235 | Deletion Frame 212-418 |
| 23 | 55 | AQPLCVPSV | 140 | Deletion Frame 212-418 |
| 24 | 1399 - 1431 | RFFQMLILYYI | 346 | (-1) |
| 25 | 1399 - 1431 | FFQMLILYYI | 313 | (-1) |
| 26 | 1399 - 1431 | FQMLILYYI | 3 | (-1) |
| 27 | 1399 - 1431 | FQMLILYYIL | 22 | (-1) |
| 28 | 1399 - 1431 | QMLILYYIL | 158 | (-1) |
| 29 | 1399 - 1431 | LILYYILPRKV | 303 | (-1) |
| 30 | 1346 - 1398 | ALDKPCHQAEV | 372 | (-1) |
| 31 | 1399 - 1431 | ILYYILPRKV | 36 | (-1) |
| 32 | 1496 - 1586 | FLPCQQSHHV | 70 | (-1) |
| 33 | 1496 - 1586 | RLLQNYLHL | 121 | (-1) |
| 34 | 1496 - 1586 | YLHLWQGNQV | 55 | (-1) |
| 35 | 1496 - 1586 | HLWQGNQVSCL | 365 | (-1) |
| 36 | 1399 - 1431 | KVLQMDFLV | 17 | (-1) |
| 37 | 1410 - 1425 | RMYYFCHANKV | 106 | (+1) |

TABLE 1-continued depicts peptide sequences of neopeptides generated from the RNF43 suppressor gene (SEQ ID NOs: 1-23) and from the APC tumor suppressor gene (SEQ ID NOs: 24-45). KD values for SEQ ID NOs: 1-23 are given for HLA-A02:01.

| SEQ ID NO: | Position or Frame position | Peptide | Kd, nM | Frame or Frame type |
|---|---|---|---|---|
| 38 | 1410 - 1425 | RMYYFCHA | 631 | (+1) |
| 39 | 1346 - 1398 | YLKIKHLLL | 699 | (-1) |
| 40 | 1426 - 1465 | CVQTSTITK | 134 | (+1) |
| 41 | 1496 - 1586 | GMICHGCIV | 118 | (-1) |
| 42 | 1496 - 1586 | GMICHGCIVL | 241 | (-1) |
| 43 | 1335 - 1360 | FLFIQPEC | 364 | (+1) |
| 44 | 1399 - 1431 | LQMDFLVHPA | 20 | (-1) |
| 45 | 1399 - 1431 | QMDFLVHPA | 55 | (-1) |

Exemplary neopeptides may also be selected from the group consisting of any one of SEQ ID NO: 58-SEQ ID NO: 62. These neopeptides are also listed in table 2 as depicted below as well as in FIG. 12.

TABLE 2 depicts peptide sequences of neopeptides generated from the RNF43 suppressor gene (SEQ ID NOs: 58-62). KD values are given for the HLA type indicated in the table.

| SEQ ID NO: | Peptide | HLA type | Kd, nM | Frame or Frame type |
|---|---|---|---|---|
| 58 | HPRSQAWAL | HLA-B0702 | 5 | (+1) |
| 59 | VPSVWRSSL | HLA-B0702 | 6 | (+1) |
| 60 | IPAMPTTTSL | HLA-B0702 | 6.5 | (+1) |
| 1 | SLLPTCWAL | HLA-A0201 | 7 | (+1) |
| 61 | RPAAGRPGV | HLA-B0702 | 13.2 | (+1) |
| 62 | APGRSPAPL | HLA-B0702 | 15 | (+2) |
| 58 | HPRSQAWAL | HLA-B0801 | 17.7 | (+1) |

The neopeptide can also be a neopeptide which can be selected from the group consisting of any one of SEQ ID NO: 1-SEQ ID NO: 23 or from the group consisting of any one of SEQ ID NO: 24-SEQ ID NO: 45 or from the group consisting of any one of SEQ ID NO: 58-SEQ ID NO: 62.

The neopeptide of the present invention can be presented by a MHC molecule e.g. an MHC monomer. In principle any MHC molecule in the art can represent a neopeptide of the present invention. For example, the MHC molecule can be a MHC class I molecule or a MHC class II molecule. The MHC class II molecule includes the HLA-DP, HLA-DQ, HLA-DR, HLA-DN or HLA-DO isotypes. MHC class I molecules include the HLA-A, HLA-B, HLA-C HLA-E, HLA-F and HLA-G isotypes. Thus, the neopeptide can be HLA-A, HLA-B or HLA-C restricted. Further, the neopeptide can be HLA class I restricted. The HLA class I restricted neopeptide may further be of a HLA-A isotype. It is also envisioned that the neopeptide of the present invention is HLA-A restricted. It is also contemplated that the neopeptide of the present invention is HLA-A2 restricted.

In line with the indications concerning isotype restricted HLA isotypes, the neopeptide can also be presentable by any of these HLA isotypes. For example, the MHC molecule can be a MHC class I molecule or a MHC class II molecule. In particular, the neopeptide can be MHC class I presentable.

The complex of the neopeptide and its presenting MHC molecule can then be detected by a T cell. Such a T cell can be a cytotoxic T cell, a regulatory T cell, a T helper cell or a NK T cell. However, the neopeptide as such may also be detected by antibodies, which have been produced from B cells.

The neopeptide used in the present invention can be expressed by or derived from a tumor suppressor gene. A "tumor suppressor gene" when used herein refers to a gene that protects a cell from carcinogenic transformation. These genes normally act to inhibit cell proliferation and tumor development. In many tumors, these genes are lost or inactivated, thereby removing negative regulators of cell proliferation and contributing to the abnormal proliferation of tumor cells. The term tumor suppressor gene is therefore meant to mean any gene that inhibits cell proliferation and tumor development. For example, such tumor suppressor genes include any of APC, BRCA1, BRAC2, DPC4, INK4, MADR2, NF1, NF2, p53, PTC, PTEN, Rb, VHL, WT1, RNF43, GATA3, NOTCH1, NPM1 or ACVR2A, ARID1A, SMAD4, CDKN2A, SLC16A4, CDC27, MYO6, MLL3, TAF1, MAP2K4, TGFBR2, ACVR1B, PREX2, ARID1B, PBRM1, SMARCA2, SMARCA4, MLL2, KDM6A, SF3B1, PALB2, RPA1, ATM, STK11, MLH1, MSH2, ROBO1, ROBO2, SLIT2, MYC, GATA6, CDK6, NOV, MET, SOX9, ERBB2, PIK3CA, PIK3R3, FGFR2. The tumor suppressor gene can also be one of RNF43, APC, WT1, ARID1A, GATA3, NOTCH1, NPM1, ACVR2A or PTEN, preferably RNF43 or APC. As for RNF43, an overview of known mutations can be obtained from the Cosmic database (http://cancer.sanger.ac.uk/cosmic). Of the 446 mutations listed in March 2016, 196 (44%) are frameshift mutations.

The tumor suppressor gene can additionally or alternatively comprises a high frameshift mutation rate. Such a frameshift mutation rate is provided as the number of mutations per cell divisions. For example a high rate of frameshift mutations can be a rate that is higher than $0.5\times10^{-5}$, $2\times10^{-5}$, $4\times10^{-5}$, $6\times10^{-5}$, $8\times10^{-5}$ or higher than $0.01\times10^{-4}$, $0.05\times10^{-5}$, $0.1\times10^{-4}$, $0.5\times10^{-4}$, $2\times10^{-4}$ or $5\times10^{-4}$.

In addition, or alternatively the tumor suppressor gene can additionally or alternatively comprise a high frameshift mutant frequency. This frequency is the ratio of mutants observed/total population analyzed (times 100 to provide for a percentage). A high frameshift mutant frequency can for example be a frequency of more than 10%, 15%, 20%, 25%, 30%, 35%, 40%, 45%, 50%, 55%, 60%, 65%, 70% or more.

It is further envisioned by the present invention that the T cell has been obtained from a subject. The term "subject" can also mean human or an animal. The subject can also be a subject suffering from cancer. The subject can be a vertebrate, more preferably a mammal. Mammals include, but are not limited to, farm animals, sport animals, pets, primates, mice and rats. Preferably, a mammal is as a human, dog, cat, cow, pig, mouse, rat etc., particularly preferred is a human being. Thus, in one embodiment, the subject is a mammal, preferably a human being. The human can be a human patient, a healthy donor or a non-healthy donor. The non-healthy donor can for example be a cancer patient.

The present invention additionally relates to a T cell capable of binding a neopeptide that is derived from a mutation in a tumor suppressor gene, wherein the binding complex of the T cell formed with the neopeptide has a half-life ($T_{1/2}$) of at least 50 s, wherein the T cell is obtainable by the method of the present invention.

Furthermore, the present invention relates to the T cell of the present invention for use in tumor specific T cell activation. The rationale behind this application is that neopeptide-specific T cells can recognize tumor cells that contain the mutation presented by the neopeptide. This recognition can then induce cytotoxic tumor cell killing. Thus, the present invention also relates to the T cell of the present invention for use in tumor cell killing.

For the T cell of the invention to become effective, this cell can also be administered to a subject. The term "administration" means administering of a therapeutically effective dose of the T cell to a subject. The term "administering" also relates to a method of incorporating the T cell into tissues of an organism. Different routes of administration are possible. The T cell or the pharmaceutical composition of the present invention can, for example, be administered via different ways such as any parenteral or non-parenteral (enteral or topical) route that is therapeutically effective for (preferably proteinaceous) drugs. Parenteral application methods include, for example, subcutaneous, intramuscular, intracerebral, intracerebroventricular, intrathecal, intranasal, intraatrial, intraperitoneal or intravenous injection and infusion techniques, e.g. in the form of injection solutions, infusion solutions or tinctures. In general, T cell and pharmaceutical compositions of the present invention can be administered in formulations containing conventional non-toxic pharmaceutically acceptable excipients or carriers, additives and vehicles as desired and described herein.

As already indicated the present invention also relates to a pharmaceutical composition comprising the T cell of the present invention and optionally pharmaceutically acceptable excipient. Accordingly, the T cell of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.).

The formulations can be sterilized by numerous means, including filtration through a bacteria-retaining filter, or by incorporating sterilizing agents in the form of sterile solid compositions which can be dissolved or dispersed in sterile water or other sterile medium just prior to use. Numerous possible applications for the T cell of the present invention exist in medicine.

A "dosage" of the T cell of the present invention applied may vary within wide limits to achieve the desired preventive effect or therapeutic response. It will, for instance, depend on the affinity/avidity of the T cell for a chosen target as well as on the half-life of the complex between a neopeptide-specific T cell and the target cell, such as a cancer cell in vivo. Further, the optimal dosage will depend on the biodistribution of the T cell of the present invention, the mode of administration, the severity of the disease/disorder being treated as well as the medical condition of the subject/patient. For example, when used in an ointment for topical applications, a high concentration of the T cells of the invention can be used.

Any suitable dosage of the T cell of the present invention can be used. It is within knowledge of the person of average skill in the art to, for example, empirically determine a suitable dosage of the T cell of the present invention.

In principle, that multiple doses of T cells are preferred to a single infusion of T cells. Doses of T cells are usually reported as the total number of viable cells administered or as the total number of viable cells administered per kilogram of body weight or per square meter of body surface area. Exemplary dosages of T cells may include or be more than about $1.46\times10^5$ to about $1.60\times10^7$ T cells cells/kg body weight of the patient, may include or be more than about 1.5 to about $3.0\times10^6$ T cells/kg body weight, may include or be more than about 0.4 to about $3.0\times10^7$ cells/kg body weight, or may include or be more than $1\times10^8/m^2$ to $3.3\times10^9)/m^2$ skin surface of the patient.

Cytokines given to the host can have a major impact on the persistence of the applied T cells. For example, the persistence of an administered T cell can be enhanced by co-administration of IL-2, IL-15 and/or IL-7.

The T cells or pharmaceutical compositions of the present invention can also be used in co-treatment with other therapies. Such a co-treatment can include administration of the T cells or pharmaceutical compositions of the present invention, preferably in the form of a medicament, to a subject suffering from a disease, such as cancer and the administration of another medicament/drug. Examples of such additional drugs are drugs used in chemotherapy, radiation therapy, angiogenesis inhibitors or cancer vaccines. Further examples of such additional drugs are thyroid supplements, vitamins such as B12, or insulin injections, immunosuppressives, such as cortisol, natalizumab or Infliximab.

The T cell used in therapy as described above can again be e.g. an expanded T cell, which has been originally isolated from a subject or a recombinantly obtained T cell.

Suitable TCR sequences, which can be used for recombinantly producing T cells of the present invention, include a TCR comprising a sequence of any of SEQ ID NO. 54-SEQ ID NO. 57. For recombinant production of a neopeptide-specific T cell a TCR comprising a TCR alpha chain (CDR3) of SEQ ID NO: 54 and a TCR beta chain (CDR3) of SEQ ID NO: 55 can be used. Alternatively or additionally for producing a neopeptide-specific T cell a TCR comprising a TCR alpha chain (CDR3) of SEQ ID NO: 56 and a TCR beta chain (CDR3) of SEQ ID NO: 57 can be used. It is also envisioned by the present invention that a TCR comprises alpha and beta chains of different T cell clones or of the same T cell clone. The present invention also relates to a T cell comprising any of SEQ ID NO. 54-SEQ ID NO. 57 for use in therapy, preferably cancer therapy. The present invention also encompasses a T cell comprising a TCR alpha chain (CDR3) of SEQ ID NO: 54 and a TCR beta chain (CDR3) of SEQ ID NO: 55. In addition, the present invention encompasses a T cell comprising a TCR alpha chain (CDR3) of SEQ ID NO: 56 and a TCR beta chain (CDR3) of SEQ ID NO: 57.

The present invention also relates to a use of the T cell of the present invention or the pharmaceutical composition of the present invention in the manufacture of a medicament for treating a subject having a disease, preferably cancer.

The term cancer, when referred to herein means any possible cancer. Exemplary types of cancer include adrenal cancer, anal cancer, bile duct cancer, bladder cancer, bone cancer, brain and spinal cord tumors, breast cancer, Castleman disease, cervical cancer, colon cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, rectum cancer, retinoblastoma, rhabdomyosarcoma, salivary gland cancer, sarcoma, skin cancer, basal and squamous cell cancer, melanoma, merkel cell cancer, small intestine cancer, stomach cancer, testicular cancer, thymus cancer, thyroid cancer, uterine sarcoma, vaginal cancer, vulvar cancer, Waldenstrom macroglobulinemia, or Wilms tumor. It has further been shown that in gastrointestinal cancers, RNF43 has above-average mutation frequencies, which can for example be seen from the cBioPortal database (www.cbioportal.org). Hence, in one embodiment, the cancer is gastrointestinal cancer. In one embodiment, cancer is colon cancer.

The present invention also relates to a method of treating cancer in a subject, comprising the step of administering the T cell of the present invention or the pharmaceutical composition of the present invention to a subject in need thereof.

The present invention also relates to a nucleic acid molecule encoding for the neopeptides or TCRs of the present invention. The nucleic acid molecule may be DNA or RNA and may be of genomic or synthetic origin and may be single or double stranded. Examples of nucleic acids include mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label, which can then also be comprised by the T cells, especially the recombinant T cells. Such an affinity tag can be an oligohistidine-tag such as his6-tag, the Flag tag, the Strep-tag®, the HA-tag, a calmodulin-tag or a GFP-tag. The nucleic acid molecules of the present invention can for example be comprised in a vector. The present invention also relates to a host cell comprising the nucleic acid molecule of the present invention or the vector as described herein.

The present invention is further characterized by the following items:

1. A method for providing a neopeptide-specific T cell, wherein the neopeptide-specific T cell forms a complex having a half-life ($T_{1/2}$) of at least 50 s with a neopeptide-MHC monomer, wherein said neopeptide is expressed by a tumor suppressor gene, the method comprising:
   a) contacting T cells with a detectably labeled neopeptide-MHC complex;
   b) isolating a T-cell, which comprises a T cell receptor (TCR) that specifically binds to the neopeptide-MHC complex or wherein the T cell is activated via binding to the neopeptide-MHC complex; and
   c) determining the $T_{1/2}$ by measuring the signal of the detectable label comprised in the MHC monomer over a period of time.
2. The method of item 1, wherein the detectable label is a fluorescent label.
3. The method of item 2, wherein the neopeptide-MHC complex is a neopeptide-MHC monomer or a neopeptide-MHC multimer.
4. The method of item 3, wherein the MHC multimer is a MHC tetramer, MHC pentamer or a MHC dextramer.
5. The method of any of items 1-4, wherein step b) further comprises
   b.1) isolating the neopeptide-specific TCR;
   b.2) determining the TCR α chain and β chain sequences;
   b.3) recombinantly expressing the neopeptide-specific TCR in a T cell.
6. The method of any of items 1-5, wherein the neopeptide-MHC monomer further comprises a streptavidin binding peptide.
7. The method of item 6, wherein the streptavidin binding peptide comprises a sequence selected from sequence is selected from Trp-Arg-His-Pro-Gln-Phe-Gly-Gly (SEQ ID NO: 46), Trp-Ser-His-Pro-Gln-Phe-Glu-Lys (SEQ ID NO: 47), Trp-Ser-His-Pro-Gln-Phe-Glu-Lys-(GlyGlyGlySer)$_3$-Trp-Ser-His-Pro-Gln-Phe-Glu-Lys (SEQ ID NO: 48), Trp-Ser-His-Pro-Gln-Phe-Glu-Lys-(GlyGlyGlySer)$_2$-Trp-Ser-His-Pro-Gln-Phe-Glu-Lys (SEQ ID NO: 49) or Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 50).
8. The method of item 6 or 7, wherein the streptavidin binding peptide is directly fused to the neopeptide-MHC monomer or conjugated via a linker to the neopeptide-MHC monomer.
9. The method of any of items 6-8, wherein the neopeptide-MHC monomer reversibly binds to a streptavidin mutein.
10. The method of any of items 6-9, wherein step c) further comprises contacting the neopeptide-MHC monomer with a streptavidin mutein.
11. The method of item 10, wherein step c) comprises c.1) contacting T cells with the neopeptide-MHC monomer and a streptavidin mutein, wherein the neopeptide-MHC monomer comprises a streptavidin binding peptide that reversibly binds to the Streptavidin mutein.

12. The method of any of items 6-11, the method further comprising
c.2) adding D-biotin.

13. The method of any of items 6-12, wherein the $T_{1/2}$ is determined performed after the addition of D-biotin.

14. The method of any of items 6-13, wherein the period of time over which the signal is measured in step c) is a period of 800 s or less, 750 s or less, 700 s or less, 650 s of less, 600 s or less, 500 s or less, 400 s or less, 300 s or less or 200 s or less.

15. The method of any of items 1-14, wherein $T_{1/2}$ is at least 55 s or more, 60 s or more, 65 s or more, 70 s or more, 75 s or more, 80 s or more, 85 s or more, 90 s or more, 95 s or more, 100 s or more, 105 s or more or 110 s or more.

16. The method of any of items 1-15, wherein step c) is performed at about 4° C.

17. The method of any of items 1-16, wherein the detectable label is a fluorescent dye, preferably Atto565.

18. The method of item 17, wherein the measured signal of the fluorescent dye is corrected for photo bleaching.

19. The method of any of items 1-18, wherein the method further comprises the step of expanding the isolated neoepitope-specific T cell obtained in step b).

20. The method of item 5, wherein isolating of the neoepitope-specific TCR is performed by PCR.

21. The method of item 20, wherein the PCR comprises
a) a gene-specific reverse transcription;
b) an anchor PCR; and
c) a nested PCR.

22. The method of item 21, wherein the gene specific reverse transcription results in cDNA transcripts.

23. The method of item 21 or 22, wherein the reverse transcription is performed at 40° C. to 80° C. for a period of time.

24. The method of item 23, wherein reverse transcription is performed with a temperature increase from 51° C. for 20 minutes to 70° C. for 30 minutes.

25. The method of any of items 20-24, wherein the gene specific reverse transcription is followed by a primer exonuclease digestion by the addition of exonuclease-I.

26. The method of item 21, wherein the anchor PCR results in an oligo-dG stretch at the 3' end of the cDNA.

27. The method of item 21, wherein the nested PCR is used to amplify the α and β chains of the TCR.

28. The method of any of items 20-27, wherein more than 3%, 5%, 7%, 10%, 13%, 15%, 17% 20% 25% of all cell samples result in the complete variable part of the TCR sequences.

29. The method of any of items 20-28, wherein the PCR protocol is started within 48 hours, 36 hours or 24 hours after T cell isolation, preferably 48 hours after T cell isolation.

30. The method of any of items 1-29, wherein the neopeptide is expressed by a tumor suppressor gene comprising a point mutation or a frameshift mutation.

31. The method of item 30, wherein the point mutation is a missense or a nonsense mutation.

32. The method of item 30, wherein the frameshift mutation is the result of an insertion or deletion.

33. The method of item 30 or 32, wherein the frameshift mutation is selected from a −5, −4, −3, −2, −1, +1, +2, +3, +4 or +5 mutation.

34. The method of any of items 1-32, wherein the neopeptide is immunogenic.

35. The method of any of items 1-33, wherein the neopeptide is a foreign epitope.

36. The method of any of items 1-34, wherein the neopeptide is selected from the group consisting of SEQ ID NO: 1-SEQ ID NO: 45 and SEQ ID NO: 58-SEQ ID NO: 62.

37. The method of any of items 1-36, wherein the neopeptide is HLA class I restricted.

38. The method of item 37, wherein the neopeptide is HLA-A, HLA-B or HLA-C, preferably HLA-A, most preferably HLA-A2 restricted.

39. The method of any of items 1-38, wherein the neopeptide is MHC class I presentable.

40. The method of any of items 1-39, wherein the T cell is a cytotoxic T cell, a regulatory T cell, a T helper cell or a NK T cell.

41. The method of any of items 1-40, wherein the tumor suppressor gene comprises a high frameshift mutation rate.

42. The method of any of items 1-41, wherein the tumor suppressor gene is one of RNF43, APC, WT1, ARID1A, GATA3, NOTCH1, NPM1, ACVR2A, PTEN, SMAD4, CDKN2A, SLC16A4, CDC27, MYO6, MLL3, TAF1, MAP2K4, TGFBR2, ACVR1B, PREX2, ARID1B, PBRM1, SMARCA2, SMARCA4, MLL2, KDM6A, SF3B1, PALB2, RPA1, ATM, STK11, MLH1, MSH2, ROBO1, ROBO2, SLIT2, MYC, GATA6, CDK6, NOV, MET, SOX9, ERBB2, PIK3CA, PIK3R3 or FGFR2, preferably RNF43 or APC.

43. The method of any of items 1-42, wherein the T cell has been obtained from a subject.

44. The method of item 43, wherein the subject is a mammal, preferably a human.

45. The method of item 44, wherein the human is a human patient, a healthy donor or a non-healthy donor.

46. The method of item 45, wherein the non-healthy donor is a cancer patient.

47. A T cell capable of binding a neopeptide that is expressed by a tumor suppressor gene, wherein the binding complex of the T cell formed with the neopeptide has a half-life (T½) of at least 50 s, wherein the T cell is obtainable by the method as defined in any of items 1-45.

48. The T cell of item 47 for use in tumor specific T cell activation.

49. The T cell of item 47 for use in tumor cell killing.

50. The T cell for use of item 48 or 49, wherein said T cell is administered to a subject.

51. A pharmaceutical composition comprising the T cell of item 47.

52. A TCR comprising a sequence of any of SEQ ID NO: 54-SEQ ID NO: 57.

53. A neopeptide of the sequence of any one of SEQ ID NO: 1-SEQ ID NO: 45 and SEQ ID NO: 58-SEQ ID NO: 62.

54. Use of the T cell as defined in item 47 or the pharmaceutical composition of item 51 in the manufacture of a medicament for treating a subject having a disease, preferably cancer.

55. A method of treating cancer in a subject, comprising the step of administering the T cell as defined in item 47 or the pharmaceutical composition of item 51 to a subject in need thereof.

The invention is further illustrated by the following non-limiting Examples.

EXAMPLE 1

Human CMV-specific T cells were purified from healthy blood donors PBMCs, stained with Strep-Tactin® Allophycocyanin (APC, blue, available from IBA GmbH Göttingen, Germany) and MHC Atto565 (red) double-labeled Streptamer® multimers, and subsequently analyzed in the $k_{off}$-rate assay setup by real time fluorescence microscopy (FIG. 1). Surprisingly, in the Streptamer® (reversible streptavidin mediated binding) complex the MHC-Atto565 fluorescence intensity of stained cells was weak. After addition of D-biotin, Strep-Tactin® APC dissociated and its fluorescence quickly decreased. In contrast, the quenched MHC-Atto565 fluorescence reached maximal intensity after Strep-Tactin®-APC removal, followed by a fluorescence decrease that reflects the dissociation of monomeric MHCs. The maximal Atto565 fluorescence facilitated the $k_{off}$-rate analysis by identifying the starting point of the dissociation of monomeric MHC molecules. In contrast, simultaneous dissociation of MHC and Strep-Tactin® during the first seconds after addition of D-biotin might complicate the analysis. Fluorescence intensities of individual cells were plotted over time and the $k_{off}$-rate and half-life time (t½) of the binding was calculated as described herein and in Nauerth et al. (2013) "TCR-ligand koff rate correlates with the protective capacity of antigen-specific CD8+ T cells for adoptive transfer." Sci Transl Med. 5(192):192ra87.

Thus, Fluorophore-coupled MHC-Streptamer multimers were used to label CMV specific T cells in the peripheral blood of chronically CMV-infected individuals. CMV-specific T cells labeled with these pMHC-Streptamer multimers were isolated by fluorescence activated cell sorting (FACS) ex vivo. the StrepTactin®-backbone was displaced from the pMHC complexes ny addition of d-Biotin. The binding strength of monovalent pMHCs to their cognate TCR is generally too low to result in stable binding and thus dissociate from the cell-surface over time. The gradual release of pMHC from the surface can observed by a decrease in fluorescence signal of pMHC.

Each datapoint depicted in FIG. 9 represents the half-life-time ($t_{1/2}$) of the interaction of a Peptide-Major Histocompatibility Complex (pMHC) with a Cytomegalovirus (CMV) specific T cell population, plotted against the concentration of the cognate peptide-epitope resulting in half-maximal IFNγ-production. The kinetics of pMHC dissociation follow an exponential decay, which can be used to calculate a $t_{1/2}$ time that is constant throughout. Plotting the $t_{1/2}$ time of CMV-specific T cell populations from different donors against the peptide concentration which stimulations the T cells to yield 50% of the maximal frequency of IFNγ-producing cells again a correlation following an exponential growth, resulting in a plateau can be observed. With $t_{1/2}$ times below the plateau the corresponding EC50 IFNγ-values are only reached with dramatically higher peptide concentrations. Therefore the $t_{1/2}$-range between the plateau and the 50%-incline of the curve is defined as the threshold area, below which TCRs lose their protective capacity.

EXAMPLE 2

Having demonstrated a correlation between the functional avidity and the $t_{1/2}$ in vitro, the correlation between the $t_{1/2}$ and in vivo functionality of T cells was analyzed. Polyclonal T cell lines A and B specific for the Listeria monocytogenes epitope $LLO_{91-99}$ were generated by in vitro restimulation with high ($10^{-6}$ M) and low ($10^{-9}$ M) peptide concentrations. In line with published data (Alexander-Miller, Leggatt, Berzofsky (1996) "Selective expansion of high- or low-avidity cytotoxic T lymphocytes and efficacy for adoptive immunotherapy." Proc Natl Acad Sci USA; 93(9):4102-7) high peptide concentration expanded low avidity T cell line A that required higher peptide concentrations for half-maximal specific lysis of target cells or half-maximal IFNγ secretion in comparison to cell line B. The avidities of the T cell lines were measured by the "Streptamer®" $K_{off}$-rate-assay. The avidity of cell-line A is characterized by a $t_{1/2}$ time of 19 s, whereas cell-line B shows a much slower pMHC dissociation of $t_{1/2}$=91 s. Cell line A or B were infused into separate mice, which were infected with Listeria the next day. Three days after infection the bacterial load in their spleens were determined. Mice, which had received cell line A had a bacterial burden in the same range as the control mice that had not received T cells at all, whereas mice that had obtained higher avid cell-line B demonstrated a significantly reduced bacterial burden.

EXAMPLE 3

Based on the above-determined threshold, neopeptide specific T-cell populations such as, for example the RNF43 frameshift neopeptide specific T cell populations shown in FIG. 4 (that were labeled with Peptide-MHC multimers after 2 weeks of in vitro expansion and that have, optionally been further analyzed with respective to their T cell receptor sequences (see FIG. 5)) or the APC frameshift neopeptide specific T cell populations shown in FIG. 8 (that were labeled with neopeptide-MHC multimers after 2 weeks of in vitro expansion) can be subjected to the kinetic characterization (determination of the half-life of their complex with a neopeptide-MHC monomer) as described herein to select those neopeptide specific T cells that form a complex having a half-life ($T_{1/2}$) of at least 50 s with a neopeptide-MHC monomer.

EXAMPLE 4

In an unbiased approach, we first wanted to screen the entire "neo-epitome" of RNF43 for possible target candidates. We therefore generated theoretical neoORFs in silico (sequence of RNF43 with an n+1 nt or n+2 nt frame shift). The MHC avidity of all possible 8 mer, 9 mer, 10 mer and 11 mer sequences of these neoORFs was predicted using NetMHC4.0 (Lundegaard et al. Nucleic Acids Research 2008, 36(Web Server issue):W509-12). Out of 4614 possible neo-epitopes, 35 (=0.8%) were predicted to have a MHC avidity of <20 nM. FIG. 12 shows seven examples of these 35 predicted neo-epitopes with a particularly high MHC binding affinity. For all of these neo-epitopes, multiple mutations have been described in the literature leading to the respective neoORF. Furthermore, it could be experimentally confirmed that each of these neo-epitopes or an elongated precursor were processed in an in vitro proteasome digestion assay (Textoris-Taube et al. JBC 2015, 290(51):30417-28). These neo-epitopes therefore represent highly promising target candidates. These neo-epitopes therefore represent highly promising target candidates against which neopeptide-specific T cells can be generated by the means of the present invention.

Unless otherwise stated, the following terms used in this document, including the description and claims, have the definitions given below.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Those skilled in the art will recognize, or be able to ascertain, using not more than routine experimentation, many equivalents to the specific embodiments of the invention described herein. Such equivalents are intended to be encompassed by the present invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

REFERENCE LIST

1. Nauerth M, Weiβbrich B, Knall R, Franz T, Dössinger G, Bet J, Paszkiewicz P J, Pfeifer L, Bunse M, Uckert W, Holtappels R, Gillert-Marien D, Neuenhahn M, Krackhardt A, Reddehase M J, Riddell S R, Busch D H. TCR-ligand koff rate correlates with the protective capacity of antigen-specific CD8+ T cells for adoptive transfer. Sci Transl Med. 2013 Jul. 3; 5(192):192ra87.

2. Ozawa T, Tajiri K, Kishi H, Muraguchi A. Comprehensive analysis of the functional TCR repertoire at the single-cell level. Biochem Biophys Res Commun. 2008 Mar. 21; 367(4):820-5.

3. Sun X, Saito M, Sato Y, Chikata T, Naruto T, Ozawa T, Kobayashi E, Kishi H, Muraguchi A, Takiguchi M. Unbiased analysis of TCRα/β chains at the single-cell level in human CD8+ T-cell subsets. PLoS One. 2012; 7(7):e40386

4. Stemberger C, Graef P, Odendahl M, Albrecht J, Dössinger G, Anderl F, Buchholz V R, Gasteiger G, Schiemann M, Grigoleit G U, Schuster F R, Borkhardt A, Versluys B, Tonn T, Seifried E, Einsele H, Germeroth L, Busch D H, Neuenhahn M. Lowest numbers of primary CD8(+) T cells can reconstitute protective immunity upon adoptive immunotherapy. Blood. 2014 Jul. 24; 124(4):628-37.

5. Alexander-Miller M A, Leggatt G R, Berzofsky J A. Selective expansion of high- or low-avidity cytotoxic T lymphocytes and efficacy for adoptive immunotherapy. Proc Natl Acad Sci USA. 1996 Apr. 30; 93(9):4102-7.

6. Patton J S, Fishburn C S, Weers J G. "The lungs as a portal of entry for systemic drug delivery." Proc. Amer. Thoracic Soc. 2004 Vol. 1 pages 338-344

7. Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science. 2006; 314:126-129

8. Alexander-Miller M A, Leggatt G R, Berzofsky J A. Selective expansion of high- or low-avidity cytotoxic T lymphocytes and efficacy for adoptive immunotherapy. Proc Natl Acad Sci USA. 1996 Apr. 30; 93(9):4102-7.

9. Rosenberg, S. A., et al., Use of tumor-infiltrating lymphocytes and interleukin-2 in the immunotherapy of patients with metastatic melanoma. A preliminary report. N Engl J Med, 1988. 319(25): p. 1676-80.

10. Rosenberg, S. A., et al., Durable complete responses in heavily pretreated patients with metastatic melanoma using T-cell transfer immunotherapy. Clin Cancer Res, 2011. 17(13): p. 4550-7.

11. Wolfel, T., et al., A p16INK4a-insensitive CDK4 mutant targeted by cytolytic T lymphocytes in a human melanoma. Science, 1995. 269(5228): p. 1281-4.

12. Tran, E., et al., Cancer immunotherapy based on mutation-specific CD4+ T cells in a patient with epithelial cancer. Science, 2014. 344(6184): p. 641-5.

13. Linnemann, C., et al., High-throughput epitope discovery reveals frequent recognition of neo-antigens by CD4+ T cells in human melanoma. Nat Med, 2015. 21(1): p. 81-5.

14. Morgan, R. A., et al., Cancer regression in patients after transfer of genetically engineered lymphocytes. Science, 2006. 314(5796): p. 126-9.

15. Robbins, P. F., et al., Tumor regression in patients with metastatic synovial cell sarcoma and melanoma using genetically engineered lymphocytes reactive with NY-ESO-1. J Clin Oncol, 2011. 29(7): p. 917-24.

16. Dössinger G, Bunse M, Bet J, Albrecht J, Paszkiewicz P J, Weiβbrich B, Schiedewitz I, Henkel L, Schiemann M, Neuenhahn M, Uckert W, Busch D H. MHC multimer-guided and cell culture-independent isolation of functional T cell receptors from single cells facilitates TCR identification for immunotherapy. PLoS One. 2013 Apr. 26; 8(4):e61384.

17. Smith-Garvin J E, Koretzky G A, Jordan M S. T cell activation. Annu Rev Immunol. 2009; 27:591-619

18. Lundegaard, C., et al., NetMHC-3.0: accurate web accessible predictions of human, mouse and monkey MHC class I affinities for peptides of length 8-11. Nucleic Acids Research, 2008; 36(Web Server issue):W509-12.

19. Textoris-Taube, K., et al., The T210M Substitution in the HLA-a* 02:01 gp100 Epitope Strongly Affects Overall Proteasomal Cleavage Site Usage and Antigen Processing. J Biol Chem, 2015; 290(51):30417-28.

---

What is claimed is:

1. A method for providing a neopeptide-specific T cell, wherein the neopeptide-specific T cell forms a complex having a half-life ($T_{1/2}$) of at least 50 s with a neopeptide-MHC monomer, wherein said neopeptide is derived from a frameshift product of a tumor suppressor gene, the method comprising:
   a) contacting a population of T cells obtained from a human subject with a detectably labeled neopeptide-MHC complex;
   b) isolating a T-cell from the population of step (a) which comprises a T cell receptor (TCR) that specifically binds to the neopeptide-MHC complex or wherein the T cell is activated via binding to the neopeptide-MHC complex to obtain neopeptide-specific T cells;
   c) determining the $T_{1/2}$ of the neopeptide-MHC complex formed by the neopeptide-specific T cells by measuring the signal of the detectable label comprised in the MHC monomer over a period of time; and
   d) selecting neopeptide-specific T cells in which the $T_{1/2}$ is at least 50 s.

2. The method of claim 1, wherein the neopeptide-MHC complex is a neopeptide-MHC monomer or a neopeptide-MHC multimer.

3. The method of claim 1, wherein step b) further comprises
  b.1) isolating the neopeptide-specific TCR;
  b.2) determining the TCR a chain and b chain sequences;
  b.3) recombinantly expressing the neopeptide-specific TCR in a T cell.

4. The method of claim 1, wherein the neopeptide-MHC monomer further comprises a streptavidin binding peptide.

5. The method of claim 4, wherein the neopeptide-MHC monomer reversibly binds to a streptavidin mutein.

6. The method of claim 4, wherein step c) further comprises contacting the neopeptide-MHC monomer with a streptavidin mutein.

7. The method of claim 1, wherein the neopeptide is expressed by a tumor suppressor gene comprising a point mutation or a frameshift mutation.

8. The method of claim 1, wherein the neopeptide is immunogenic.

9. The method of claim 1, wherein the neopeptide is a non-self epitope.

10. The method of claim 1, wherein the neopeptide is selected from the group consisting of SEQ ID NO: 1-SEQ ID NO: 45 and SEQ ID NO: 58-SEQ ID NO: 62.

11. The method of claim 1, wherein the neopeptide is HLA class I restricted.

12. The method of claim 1, wherein the neopeptide is MHC class I presentable.

13. The method of claim 1, wherein the T cell is a cytotoxic T cell, a regulatory T cell, a T helper cell or a NK T cell.

14. The method of claim 1, wherein the tumor suppressor gene comprises a high frameshift mutation rate.

15. The method of claim 1, wherein the tumor suppressor gene is one of RNF43, APC, WT1, ARID1A, GATA3, NOTCH1, NPM1, ACVR2A, PTEN, SMAD4, CDKN2A, SLC16A4, CDC27, MYO6, MLL3, TAF1, MAP2K4, TGFBR2, ACVR1B, PREX2, ARID1B, PBRM1, SMARCA2, SMARCA4, MLL2, KDM6A, SF3B1, PALB2, RPA1, ATM, STK11, MLH1, MSH2, ROBO1, ROBO2, SLIT2, MYC, GATA6, CDK6, NOV, MET, SOX9, ERBB2, PIK3CA, PIK3R3 or FGFR2, preferably RNF43 or APC.

16. The method of claim 1, wherein the subject is a healthy donor or a non-healthy donor.

17. The method of claim 16, wherein the non-healthy donor is a cancer patient.

18. A T cell capable of binding a neopeptide that is expressed by a tumor suppressor gene, wherein said neopeptide is derived from a frameshift product of a tumor suppressor gene and wherein the T-cell binds to the neopeptide-MHC complex with a half-life ($T_{1/2}$) of at least 50 s, wherein the T cell is obtained by the method as defined in claim 1.

* * * * *

SEQUENCE LISTING

```
<160> NUMBER OF SEQ ID NOS: 62

<210> SEQ ID NO 1
<211> LENGTH: 9
<212> TYPE: PRT
<213> ORGANISM: Artificial Sequence
<220> FEATURE:
<223> OTHER INFORMATION: neopeptide

<400> SEQUENCE: 1

Ser Leu Leu Pro Thr Cys Trp Ala Leu
1               5

<210> SEQ ID NO 2
<211> LENGTH: 9
<212> TYPE: PRT
<213> ORGANISM: Artificial Sequence
<220> FEATURE:
<223> OTHER INFORMATION: neopeptide

<400> SEQUENCE: 2

Ala Met Pro Thr Thr Thr Ser Leu Leu
1               5

<210> SEQ ID NO 3
<211> LENGTH: 11
<212> TYPE: PRT
<213> ORGANISM: Artificial Sequence
<220> FEATURE:
<223> OTHER INFORMATION: neopeptide

<400> SEQUENCE: 3

Leu Leu Pro Thr Cys Trp Ala Leu Pro Gly Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: neopeptide

<400> SEQUENCE: 4

Ala Leu Gly Ile Thr Ala Ser Pro Glu Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: neopeptide

<400> SEQUENCE: 5
```

```
Ser Leu Thr Ser Leu Arg Ile Glu Leu
1               5

<210> SEQ ID NO 6
<211> LENGTH: 10
<212> TYPE: PRT
<213> ORGANISM: Artificial Sequence
<220> FEATURE:
<223> OTHER INFORMATION: neopeptide

<400> SEQUENCE: 6

Val Leu Ser Ser Leu Thr Ser Leu Arg Ile
1               5                   10

<210> SEQ ID NO 7
<211> LENGTH: 10
<212> TYPE: PRT
<213> ORGANISM: Artificial Sequence
<220> FEATURE:
<223> OTHER INFORMATION: neopeptide

<400> SEQUENCE: 7

Ser Leu Thr Ser Leu Arg Ile Glu Leu Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: neopeptide

<400> SEQUENCE: 8

Thr Gln Leu Ala Arg Phe Phe Pro Ile
1               5

<210> SEQ ID NO 9
<211> LENGTH: 9
<212> TYPE: PRT
<213> ORGANISM: Artificial Sequence
<220> FEATURE:
<223> OTHER INFORMATION: neopeptide

<400> SEQUENCE: 9

Arg Phe Phe Pro Ile Thr Pro Pro Val
1               5

<210> SEQ ID NO 10
<211> LENGTH: 9
<212> TYPE: PRT
<213> ORGANISM: Artificial Sequence
<220> FEATURE:
<223> OTHER INFORMATION: neopeptide

<400> SEQUENCE: 10

Trp Leu Ala Arg Leu Gly Trp Arg Val
1               5

<210> SEQ ID NO 11
<211> LENGTH: 9
<212> TYPE: PRT
<213> ORGANISM: Artificial Sequence
<220> FEATURE:
<223> OTHER INFORMATION: neopeptide

<400> SEQUENCE: 11
```

Ser Leu Ser Gln Pro Leu Ala Gln Leu
1               5

<210> SEQ ID NO 12
<211> LENGTH: 10
<212> TYPE: PRT
<213> ORGANISM: Artificial Sequence
<220> FEATURE:
<223> OTHER INFORMATION: neopeptide

<400> SEQUENCE: 12

Gln Leu Thr Pro Pro Ala Ser Ala Pro Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: neopeptide

<400> SEQUENCE: 13

Arg Leu Gly Trp Arg Val Ser Glu Glu Pro Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: neopeptide

<400> SEQUENCE: 14

Ala Gln Leu Thr Pro Pro Ala Ser Ala Pro Val
1               5                   10

<210> SEQ ID NO 15
<211> LENGTH: 9
<212> TYPE: PRT
<213> ORGANISM: Artificial Sequence
<220> FEATURE:
<223> OTHER INFORMATION: neopeptide

<400> SEQUENCE: 15

Leu Thr Pro Pro Ala Ser Ala Pro Val
1               5

<210> SEQ ID NO 16
<211> LENGTH: 9
<212> TYPE: PRT
<213> ORGANISM: Artificial Sequence
<220> FEATURE:
<223> OTHER INFORMATION: neopeptide

<400> SEQUENCE: 16

Ser Met Ala Ala Val Leu Leu Ser Ala
1               5

<210> SEQ ID NO 17
<211> LENGTH: 10
<212> TYPE: PRT
<213> ORGANISM: Artificial Sequence
<220> FEATURE:
<223> OTHER INFORMATION: neopeptide

<400> SEQUENCE: 17

Ser Met Ala Ala Val Leu Leu Ser Ala Ala

```
1               5                    10

<210> SEQ ID NO 18
<211> LENGTH: 9
<212> TYPE: PRT
<213> ORGANISM: Artificial Sequence
<220> FEATURE:
<223> OTHER INFORMATION: neopeptide

<400> SEQUENCE: 18

Val Leu Asp Gly Pro Pro Ala Pro Ala
1               5

<210> SEQ ID NO 19
<211> LENGTH: 10
<212> TYPE: PRT
<213> ORGANISM: Artificial Sequence
<220> FEATURE:
<223> OTHER INFORMATION: neopeptide

<400> SEQUENCE: 19

Ser Ala Tyr Arg Gly Ser Met Ala Ala Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: neopeptide

<400> SEQUENCE: 20

Arg Val Leu Asp Gly Pro Pro Ala Pro Ala
1               5                   10

<210> SEQ ID NO 21
<211> LENGTH: 10
<212> TYPE: PRT
<213> ORGANISM: Artificial Sequence
<220> FEATURE:
<223> OTHER INFORMATION: neopeptide

<400> SEQUENCE: 21

Tyr Ile Ser Ile Gly Leu Ala Pro Ser Ala
1               5                   10

<210> SEQ ID NO 22
<211> LENGTH: 9
<212> TYPE: PRT
<213> ORGANISM: Artificial Sequence
<220> FEATURE:
<223> OTHER INFORMATION: neopeptide

<400> SEQUENCE: 22

Ala Ser Met Ser Ser Ile Val Thr Val
1               5

<210> SEQ ID NO 23
<211> LENGTH: 9
<212> TYPE: PRT
<213> ORGANISM: Artificial Sequence
<220> FEATURE:
<223> OTHER INFORMATION: neopeptide

<400> SEQUENCE: 23

Ala Gln Pro Leu Cys Val Pro Ser Val
1               5
```

<210> SEQ ID NO 24
<211> LENGTH: 11
<212> TYPE: PRT
<213> ORGANISM: Artificial Sequence
<220> FEATURE:
<223> OTHER INFORMATION: neopeptide

<400> SEQUENCE: 24

Arg Phe Phe Gln Met Leu Ile Leu Tyr Tyr Ile
1               5                   10

<210> SEQ ID NO 25
<211> LENGTH: 10
<212> TYPE: PRT
<213> ORGANISM: Artificial Sequence
<220> FEATURE:
<223> OTHER INFORMATION: neopeptide

<400> SEQUENCE: 25

Phe Phe Gln Met Leu Ile Leu Tyr Tyr Ile
1               5                   10

<210> SEQ ID NO 26
<211> LENGTH: 9
<212> TYPE: PRT
<213> ORGANISM: Artificial Sequence
<220> FEATURE:
<223> OTHER INFORMATION: neopeptide

<400> SEQUENCE: 26

Phe Gln Met Leu Ile Leu Tyr Tyr Ile
1               5

<210> SEQ ID NO 27
<211> LENGTH: 10
<212> TYPE: PRT
<213> ORGANISM: Artificial Sequence
<220> FEATURE:
<223> OTHER INFORMATION: neopeptide

<400> SEQUENCE: 27

Phe Gln Met Leu Ile Leu Tyr Tyr Ile Leu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: neopeptide

<400> SEQUENCE: 28

Gln Met Leu Ile Leu Tyr Tyr Ile Leu
1               5

<210> SEQ ID NO 29
<211> LENGTH: 11
<212> TYPE: PRT
<213> ORGANISM: Artificial Sequence
<220> FEATURE:
<223> OTHER INFORMATION: neopeptide

<400> SEQUENCE: 29

Leu Ile Leu Tyr Tyr Ile Leu Pro Arg Lys Val
1               5                   10

```
<210> SEQ ID NO 30
<211> LENGTH: 11
<212> TYPE: PRT
<213> ORGANISM: Artificial Sequence
<220> FEATURE:
<223> OTHER INFORMATION: neopeptide

<400> SEQUENCE: 30

Ala Leu Asp Lys Pro Cys His Gln Ala Glu Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: neopeptide

<400> SEQUENCE: 31

Ile Leu Tyr Tyr Ile Leu Pro Arg Lys Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: neopeptide

<400> SEQUENCE: 32

Phe Leu Pro Cys Gln Gln Ser His His Val
1               5                   10

<210> SEQ ID NO 33
<211> LENGTH: 9
<212> TYPE: PRT
<213> ORGANISM: Artificial Sequence
<220> FEATURE:
<223> OTHER INFORMATION: neopeptide

<400> SEQUENCE: 33

Arg Leu Leu Gln Asn Tyr Leu His Leu
1               5

<210> SEQ ID NO 34
<211> LENGTH: 10
<212> TYPE: PRT
<213> ORGANISM: Artificial Sequence
<220> FEATURE:
<223> OTHER INFORMATION: neopeptide

<400> SEQUENCE: 34

Tyr Leu His Leu Trp Gln Gly Asn Gln Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: neopeptide

<400> SEQUENCE: 35

His Leu Trp Gln Gly Asn Gln Val Ser Cys Leu
1               5                   10
```

```
<210> SEQ ID NO 36
<211> LENGTH: 9
<212> TYPE: PRT
<213> ORGANISM: Artificial Sequence
<220> FEATURE:
<223> OTHER INFORMATION: neopeptide

<400> SEQUENCE: 36

Lys Val Leu Gln Met Asp Phe Leu Val
1               5

<210> SEQ ID NO 37
<211> LENGTH: 11
<212> TYPE: PRT
<213> ORGANISM: Artificial Sequence
<220> FEATURE:
<223> OTHER INFORMATION: neopeptide

<400> SEQUENCE: 37

Arg Met Tyr Tyr Phe Cys His Ala Asn Lys Val
1               5                   10

<210> SEQ ID NO 38
<211> LENGTH: 8
<212> TYPE: PRT
<213> ORGANISM: Artificial Sequence
<220> FEATURE:
<223> OTHER INFORMATION: neopeptide

<400> SEQUENCE: 38

Arg Met Tyr Tyr Phe Cys His Ala
1               5

<210> SEQ ID NO 39
<211> LENGTH: 9
<212> TYPE: PRT
<213> ORGANISM: Artificial Sequence
<220> FEATURE:
<223> OTHER INFORMATION: neopeptide

<400> SEQUENCE: 39

Tyr Leu Lys Ile Lys His Leu Leu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: neopeptide

<400> SEQUENCE: 40

Cys Val Gln Thr Ser Thr Ile Thr Lys
1               5

<210> SEQ ID NO 41
<211> LENGTH: 9
<212> TYPE: PRT
<213> ORGANISM: Artificial Sequence
<220> FEATURE:
<223> OTHER INFORMATION: neopeptide

<400> SEQUENCE: 41

Gly Met Ile Cys His Gly Cys Ile Val
1               5

<210> SEQ ID NO 42
```

```
<211> LENGTH: 10
<212> TYPE: PRT
<213> ORGANISM: Artificial Sequence
<220> FEATURE:
<223> OTHER INFORMATION: neopeptide

<400> SEQUENCE: 42

Gly Met Ile Cys His Gly Cys Ile Val Leu
1               5                   10

<210> SEQ ID NO 43
<211> LENGTH: 8
<212> TYPE: PRT
<213> ORGANISM: Artificial Sequence
<220> FEATURE:
<223> OTHER INFORMATION: neopeptide

<400> SEQUENCE: 43

Phe Leu Phe Ile Gln Pro Glu Cys
1               5

<210> SEQ ID NO 44
<211> LENGTH: 10
<212> TYPE: PRT
<213> ORGANISM: Artificial Sequence
<220> FEATURE:
<223> OTHER INFORMATION: neopeptide

<400> SEQUENCE: 44

Leu Gln Met Asp Phe Leu Val His Pro Ala
1               5                   10

<210> SEQ ID NO 45
<211> LENGTH: 9
<212> TYPE: PRT
<213> ORGANISM: Artificial Sequence
<220> FEATURE:
<223> OTHER INFORMATION: neopeptide

<400> SEQUENCE: 45

Gln Met Asp Phe Leu Val His Pro Ala
1               5

<210> SEQ ID NO 46
<211> LENGTH: 8
<212> TYPE: PRT
<213> ORGANISM: Artificial Sequence
<220> FEATURE:
<223> OTHER INFORMATION: streptavidin binding peptide

<400> SEQUENCE: 46

Trp Arg His Pro Gln Phe Gly Gly
1               5

<210> SEQ ID NO 47
<211> LENGTH: 8
<212> TYPE: PRT
<213> ORGANISM: Artificial Sequence
<220> FEATURE:
<223> OTHER INFORMATION: streptavidin binding peptide

<400> SEQUENCE: 47

Trp Ser His Pro Gln Phe Glu Lys
1               5

<210> SEQ ID NO 48
<211> LENGTH: 28
```

<212> TYPE: PRT
<213> ORGANISM: Artificial Sequence
<220> FEATURE:
<223> OTHER INFORMATION: streptavidin binding peptide

<400> SEQUENCE: 48

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 49
<211> LENGTH: 24
<212> TYPE: PRT
<213> ORGANISM: Artificial Sequence
<220> FEATURE:
<223> OTHER INFORMATION: streptavidin binding peptide

<400> SEQUENCE: 49

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 50
<211> LENGTH: 28
<212> TYPE: PRT
<213> ORGANISM: Artificial Sequence
<220> FEATURE:
<223> OTHER INFORMATION: streptavidin binding peptide

<400> SEQUENCE: 50

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 51
<211> LENGTH: 20
<212> TYPE: PRT
<213> ORGANISM: Artificial Sequence
<220> FEATURE:
<223> OTHER INFORMATION: signal peptide of beta 2 microglobulin

<400> SEQUENCE: 51

Met Ser Arg Ser Val Ala Leu Ala Val Leu Ala Leu Leu Ser Leu Ser
1               5                   10                  15

Gly Leu Glu Ala
            20

<210> SEQ ID NO 52
<211> LENGTH: 99
<212> TYPE: PRT
<213> ORGANISM: Artificial Sequence
<220> FEATURE:
<223> OTHER INFORMATION: beta 2 microglobulin without signal peptide

<400> SEQUENCE: 52

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

```
Val Glu His Ser Asp Leu Ser Phe Ser Lys Asp Trp Ser Phe Tyr Leu
 50                  55                  60

Leu Tyr Tyr Thr Glu Phe Thr Pro Thr Glu Lys Asp Glu Tyr Ala Cys
 65                  70                  75                  80

Arg Val Asn His Val Thr Leu Ser Gln Pro Lys Ile Val Lys Trp Asp
                 85                  90                  95

Arg Asp Met

<210> SEQ ID NO 53
<211> LENGTH: 5
<212> TYPE: PRT
<213> ORGANISM: Artificial Sequence
<220> FEATURE:
<223> OTHER INFORMATION: oligo-dG stretch

<400> SEQUENCE: 53

Gly Gly Gly Gly Gly
1               5

<210> SEQ ID NO 54
<211> LENGTH: 11
<212> TYPE: PRT
<213> ORGANISM: Artificial Sequence
<220> FEATURE:
<223> OTHER INFORMATION: TCR CDR3 sequence

<400> SEQUENCE: 54

Cys Ala Leu Thr Gly Tyr Gln Lys Val Thr Phe
1               5                   10

<210> SEQ ID NO 55
<211> LENGTH: 13
<212> TYPE: PRT
<213> ORGANISM: Artificial Sequence
<220> FEATURE:
<223> OTHER INFORMATION: TCR CD3 sequence

<400> SEQUENCE: 55

Cys Ala Ser Ser Leu Val Glu Thr Asp Ile Gln Tyr Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: TCR CDR3 sequence

<400> SEQUENCE: 56

Cys Ala Tyr Ile Val Asn Asn Asn Asp Met Arg Phe
1               5                   10

<210> SEQ ID NO 57
<211> LENGTH: 14
<212> TYPE: PRT
<213> ORGANISM: Artificial Sequence
<220> FEATURE:
<223> OTHER INFORMATION: TCR CDR3 sequence

<400> SEQUENCE: 57

Cys Ala Ser Ser Ser Trp Thr Gly Gly Tyr Glu Gln Tyr Phe
1               5                   10

<210> SEQ ID NO 58
```

```
<211> LENGTH: 9
<212> TYPE: PRT
<213> ORGANISM: Artificial Sequence
<220> FEATURE:
<223> OTHER INFORMATION: neopeptide

<400> SEQUENCE: 58

His Pro Arg Ser Gln Ala Trp Ala Leu
1               5

<210> SEQ ID NO 59
<211> LENGTH: 9
<212> TYPE: PRT
<213> ORGANISM: Artificial Sequence
<220> FEATURE:
<223> OTHER INFORMATION: neopeptide

<400> SEQUENCE: 59

Val Pro Ser Val Trp Arg Ser Ser Leu
1               5

<210> SEQ ID NO 60
<211> LENGTH: 10
<212> TYPE: PRT
<213> ORGANISM: Artificial Sequence
<220> FEATURE:
<223> OTHER INFORMATION: neopeptide

<400> SEQUENCE: 60

Ile Pro Ala Met Pro Thr Thr Thr Ser Leu
1               5                   10

<210> SEQ ID NO 61
<211> LENGTH: 9
<212> TYPE: PRT
<213> ORGANISM: Artificial Sequence
<220> FEATURE:
<223> OTHER INFORMATION: neopeptide

<400> SEQUENCE: 61

Arg Pro Ala Ala Gly Arg Pro Gly Val
1               5

<210> SEQ ID NO 62
<211> LENGTH: 9
<212> TYPE: PRT
<213> ORGANISM: Artificial Sequence
<220> FEATURE:
<223> OTHER INFORMATION: neopeptide

<400> SEQUENCE: 62

Ala Pro Gly Arg Ser Pro Ala Pro Leu
1               5
```